US006538028B1

United States Patent
Pierson, III et al.

(10) Patent No.: US 6,538,028 B1
(45) Date of Patent: Mar. 25, 2003

(54) METHOD FOR INHIBITING COMPLEMENT ACTIVATION

(75) Inventors: Richard N. Pierson, III, Nashville, TN (US); George L. Zorn, III, Nashville, TN (US); Todd D. Giorgio, Nashville, TN (US); Simon Robson, Weston, MA (US); Agnes M. Azimzadeh, Brentwood, TN (US)

(73) Assignees: Vanderbilt University, Nashville, TN (US); Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/775,094

(22) Filed: Feb. 1, 2001

Related U.S. Application Data

(60) Provisional application No. 60/179,543, filed on Feb. 1, 2000.

(51) Int. Cl.$^7$ ...................... A61K 31/195; A61K 31/19; A61K 31/70; A61K 38/16; A61K 38/00

(52) U.S. Cl. ...................... 514/564; 514/570; 514/557; 514/12; 514/8; 514/44; 514/21; 514/567

(58) Field of Search .............................. 514/12, 8, 570, 514/557, 44, 21, 567; 424/130.1, 134.1, 135.1, 136.1, 137.1, 141.1, 158.1

(56) References Cited

U.S. PATENT DOCUMENTS

| | | |
|---|---|---|
| 4,007,270 A | 2/1977 | Bernstein et al. |
| 4,880,788 A | 11/1989 | Moake et al. |
| 5,135,916 A | 8/1992 | Sims et al. |
| 5,434,185 A | 7/1995 | Collings et al. |
| 5,550,108 A | 8/1996 | Sims et al. |
| 5,573,940 A | 11/1996 | Sims et al. |
| 5,635,178 A | 6/1997 | Sims et al. |
| 5,660,825 A | 8/1997 | Sims et al. |
| 5,679,345 A | * 10/1997 | Sanfilippo et al. ....... 424/130.1 |
| 5,763,156 A | 6/1998 | Sims et al. |
| 5,858,963 A | 1/1999 | Hawley et al. |
| 5,891,645 A | 4/1999 | Rollins et al. |
| 5,955,441 A | 9/1999 | Sims et al. |

FOREIGN PATENT DOCUMENTS

| | | |
|---|---|---|
| DE | 43 38 793 A1 | 5/1995 |
| EP | 0 251 134 | 7/1988 |
| JP | 07196650 | 8/1995 |

OTHER PUBLICATIONS

Ekre, Hans–Peter, "Inhibition of Human and Guinea Pig Complement by Heparin Fractions Differing in Affinity for Antithrombin III or in Average Molecular Weight," International Journal of Immunopharmacology (Elmsford, NY, US), vol. 7 (No. 2),p. 271–275, ( Sep. 21, 1984).

Bach, et al., "Delayed xenograft rejection," Immunol. Today, Elsevier Publications (Cambridge, GB), vol. 17 ( No. 8), p. 379–384, ( Aug. 1, 1996).

Dorling, et al., "Clinical xenotransplantation of solid organs," The Lancet, p. 867–871, ( Mar. 22, 1997).

Hoelschermann, et al., "Evaluation of Recombinant Hirudin in the Prevention of Experimental Cardiac Transplant Vasculopathy," ( Nov. 2, 1999).

"The effects of cyclosporin A, ticlopidine hydrochloride and cobra venom factor on the hyperacute rejection of discocrodant renal xenografts", Green et al, 1980, Investigative and Cell Pathology, 3(4), 415–416.*

"Platelet Thrombus Formation on injured Endothelial Cell Monolayers", Nollert et al., www.aiche.org, 1999.*

"Cardiovascular Pharmacotherapy in Patients following Myocardial Infarction–the Role of Anti–platelet Agents, Anti–coagulants and Angiotensin Converting Enzyme Inhibitors", Yu–An Ding, Chin Med J (Taipei) 1996;57;S232–4.*

"Inhibition of von Willebrand Factor Binding to Platelet GP lb by a Fractionated Aurintricarboxylic Acid Prevents Restenosis After Vascular Injury in Hamster Carotid Artery", Matsuno et al., 1997, 96:1299–1304.*

Bode et al., "Plasmin Activity and Complement Activation During Storage of Citrated Platelet Concentrates," J. Lab. Clin. Red., vol. 113 (No. 1), p. 94–102, (1989).

Bruggemann et al., "Strategies for Expressing Himan Antibody Repertoires in Transgenic Mice," Immunol. Today, vol. 17 (No. 8), p. 391–397, (Aug. 1996).

Campbell, "Nuclear Transfer in Farm Animal Species," Semin. Cell. Dev. Biol., vol. 10 (No. 3), p. 245–252, (Jun. 1999).

Cibelli et al., "Cloned Transgenic Calves Produced from Nonquiescent Fetal Fibroblasts," Science, vol. 280 (No. 5367), p. 1256–1258, (May 22, 1998).

Coller et al., "New Antiplatelet Agents: Platelet GPIIb/IIIa Antagonists," Thrombosis and Haomostasis, vol. 74 (No. 1), p. 302–308, (1995).

Girma et al., "Aurin Tricarboxylic Acid Inhibits Platelet Adhesion to Collagen by Binding to the 509–695 Disulphide Loop of von Willebrand Factor and Competing with Glycoprotein Ib," p. 707–713, (1992).

Jakobovits, "Production of Fully Human Antibodies by Transgenic Mice," Curr. Opin. Biotechnol., vol. 6 (No. 5), p. 561–566, (Oct. 1995).

(List continued on next page.)

Primary Examiner—Zohreh Fay
Assistant Examiner—Brian-Yong S. Kwon
(74) Attorney, Agent, or Firm—Jenkins & Wilson, P.A.

(57) ABSTRACT

A method of inhibiting complement activation, particularly by a transplanted tissue, in a warm-blooded vertebrate. The method includes administering a therapeutically effective amount of a platelet activity modulator to a warm-blooded vertebrate before, during or after a tissue is transplanted to the warm-blooded vertebrate, whereby complement activation by the transplanted tissue is inhibited. The platelet activity modulator can include a combination of a GPIb modulator and a GPIIb/GPIIIa modulator.

21 Claims, 1 Drawing Sheet

OTHER PUBLICATIONS

King et al., "Will Blocking the Plately Save the Diabetic?," Circulation, vol. 100, p. 2466–2468, (1999).

Lonberg et al., "Human Antibodies from Transgenic Mice," Imt. Rev. Immunol., vol. 13 (No. 1), p. 65–93, (1995).

Neuberger et al., "Monoclonal Antibodies. Mice Perform a Human Repertoire,"Nature, vol. 386 (No. 6620), p. 25–26, (Mar. 6, 1997).

Nguyen et al., "Production of Human Monoclonal Antibodies in SCID Mouse," Microbiol. Immunol., vol. 41 (No. 12), p. 901–907, (1997).

Nurden et al., "Platelet Glycoprotein IIb/IIIa Inhibitors," Arterioscler. Thromb. Vasc. Biol., p. 2835–2840, (1999).

Schnieke et al., "Human Factor IX Transgenic Sheep Produced by Transfer of Nuclei from Transfected Fetal Fibroblasts," Science, vol. 278 (No. 5346), p. 2130–2133, (Dec. 19, 1997).

Sims et al., "Regulatory Control of Complement on Blood Platelets," The Journal of Biological Chemistry, vol. 264 (No. 32), p. 19228–19235, (Nov. 15, 1989).

Sundsmo et al., "Complement Activation in Type 1 Human Diabetes," Clin. Immunol. Immunopathol., vol. 35 (No. 2), p. 211–225, (May 1985).

* cited by examiner

METHOD FOR INHIBITING COMPLEMENT ACTIVATION

CROSS REFERENCE TO RELATED APPLICATIONS

This application is based on and claims priority to U.S. Provisional Application Serial No. 60/179,543, filed Feb. 1, 2000, herein incorporated by reference in its entirety.

TECHNICAL FIELD

The present invention pertains generally to modulation of activation of the complement system. More particularly, the present invention pertains to the inhibition of complement activation through the inhibition of platelet receptors for thrombin/fibrinogen. In a preferred embodiment, the present invention pertains to a method of inhibiting of transplant rejection by blocking complement activation in a recipient.

| Table of Abbreviations | |
|---|---|
| ATA | aurintricarboxylic acid |
| C | complement, usually followed by a number from 1 to 9 when referencing the factors of the complement system in the immune system |
| C3a | complement activation factor |
| C5b–9 | complement activation factors |
| CDR | complementarity determining region |
| CVF | cobra venom factor |
| Fg | fibrinogen |
| Fn | fibronectin |
| GPIb | platelet receptor involved in platelet activation and aggregation |
| GPIIb/IIIa | platelet receptor involved in platelet activation and aggregation |
| HAR | hyperacute rejection |
| HCl | hydrochloric acid |
| PPP | platelet poor plasma |
| PRP | platelet rich plasma |
| PVR | pulmonary vascular resistance |
| SC52012A | selective potent GPIIb/IIIa antagonist |
| TFA | trifluoroacetic acid |
| TXA2 | thromboxane |
| vWF | von Willebrand's Factor |

BACKGROUND ART

The complement system is a complex interaction of plasma proteins and membrane cofactors which act in a multi-step, multi-protein cascade sequence in conjunction with other immunological systems of the body to provide immunity from intrusion of foreign cells. Complement proteins represent up to about 10% of globulins in normal serum of man and other vertebrate's. The term "complement" refers to the non-specific defense system that is activated by the bonding of antibodies to antigens and by this event is directed against specific invaders that have been identified by antibodies.

Organ procurement currently poses one of the major problems in organ transplantation, as the number of patients requiring transplants far exceeds the number of organs available. Moreover, a transplanted organ is often rejected by the recipient's body. Thus, even when an organ is available, transplant rejection presents a continuing problem.

Xenotransplantation may provide a solution to the shortage of organs for transplant. Phylogenetically, non-human primates are the most closely related species to humans and might therefore represent the first choice as donors. In 1969, Reetsma et al. achieved the first successful kidney human xenograft from a chimpanzee (Reetsma, K., et al., 1964, Ann. Surg. 160:384). However, the potential utilization of primate donors is limited by insufficient numbers, legal and ethical considerations, and the potential for transmitting dangerous viral diseases. Swine represent one of the few large animal species in which breeding characteristics make genetic experiments possible, making it possible to develop MHC homozygous lines of miniature swine, for example. Miniature swine can be maintained at maximum adult weights of 200 to 300 lbs and are anatomically and physiologically close to humans. Therefore, the organs of miniature swine seem appropriate for use as xenografts for human beings of all ages.

However, problems associated with transplant rejection also persist with respect to xenograft organs from swine and from other donors. Therefore, there remains a continuing and long-felt need for therapeutic methods that inhibit transplant rejection and that faciliate the use of xenograftt organs in transplant procedures.

SUMMARY OF THE INVENTION

A method of modulating complement activation in a warm-blooded vertebrate is disclosed. The method comprises administering a therapeutically effective amount of a platelet activity modulator to a warm-blooded vertebrate, whereby complement activation is modulated. The platelet activity modulator preferably comprises a combination of a GPIb modulator and a GPIIb/GPIIIa modulator.

A method of inhibiting complement activation by a transplanted tissue in a warm-blooded vertebrate is also disclosed. The method comprises administering a therapeutically effective amount of a platelet activity modulator to a warm-blooded vertebrate before, during or after a tissue is transplanted to the warm-blooded vertebrate, whereby complement activation, by the transplanted tissue is inhibited. The platelet activity modulator preferably comprises a combination of a GPIb modulator and a GPIIb/GPIIIa modulator.

The therapeutically effective amount of the platelet activity modulator ranges from about 0.01 mg to about 10,000 mg per day, preferably from about 0.1 mg to about 1,000 mg per day, and more preferably from about 1 mg to about 300 mg per day.

The transplanted tissue can be a vascularized tissue. The vascularized tissue can include, but is not limited to heart, lung, liver, kidney, pancreas and combinations thereof.

The transplanted tissue can be xenograft tissue. The xenograft tissue can be vascularized xenograft tissue. The vascularized xenograft tissue can include, but is not limited to, heart, lung, liver, kidney, pancreas and combinations thereof. Optionally, the xenograft tissue is obtained from a donor animal having a deficient platelet activity pathway.

A method of inhibiting rejection of a transplanted tissue in a warm-blooded vertebrate is also disclosed. The method comprises administering a therapeutically effective amount of a GPIb modulator and a GPIIb/GPIIIa modulator to a warm-blooded vertebrate before, during or after a tissue is transplanted to the warm-blooded vertebrate, whereby rejection of the transplanted tissue is inhibited.

A method of enhancing tolerance of a xenograft transplant in a recipient is also disclosed. The method comprises administering a therapeutically effective amount of a GPIb modulator and a GPIIb/GPIIIa modulator to a recipient before, during or after the recipient receives a xenograft transplant, whereby tolerance of the xenograft transplant is enhanced.

Accordingly, it is an object of the present invention to provide a novel method for inhibiting transplant rejection. This and other objects are achieved in whole or in part by the present invention.

An object of the invention having been stated hereinabove, other objects will become evident as the description proceeds when taken in connection with the accompanying Drawings and Laboratory Examples as best described hereinbelow.

DETAILED DESCRIPTION OF THE INVENTION

Figure 1A:
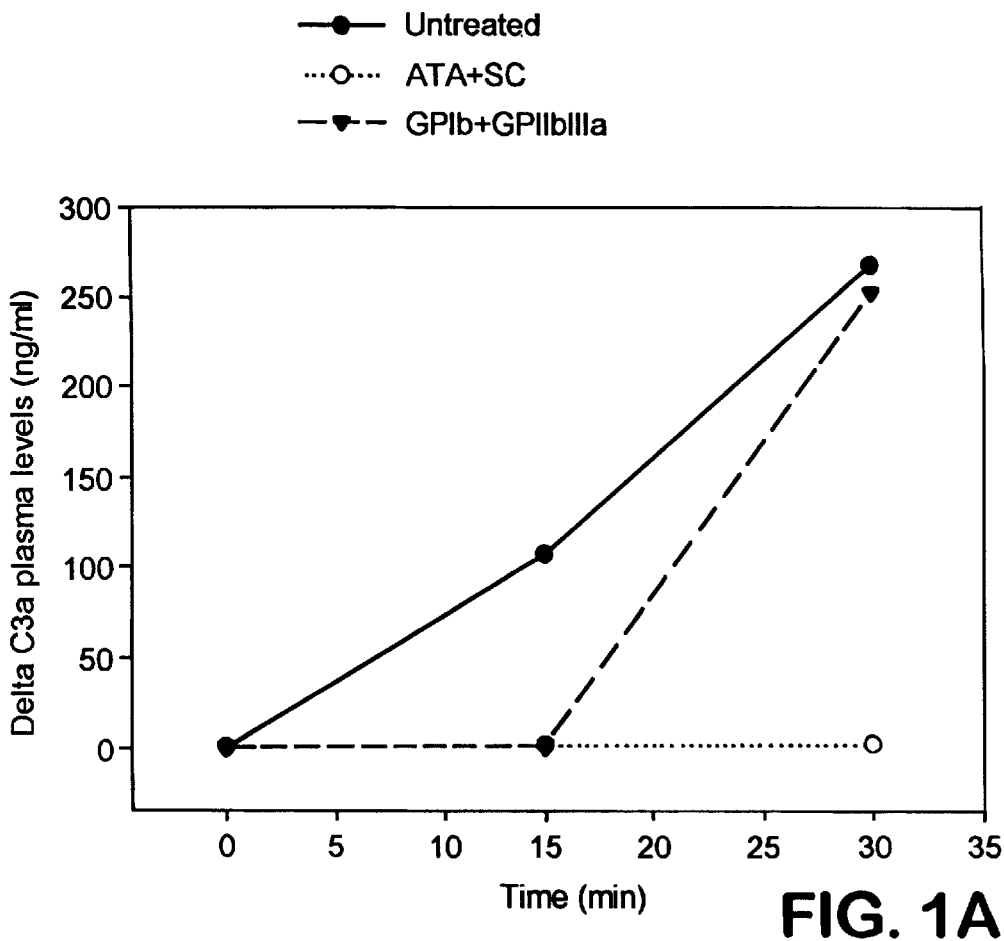
FIGS. 1A and 1B are graphs of the change (delta) in C3a plasma levels (ng/ml) versus time in minutes for the experiment described in Example 6 (●=untreated; ○=ATA+SC; ▼=GPIb+GPIIbIIIa monoclonal antibody).

The present invention pertains generally to modulation of activation of the complement system. More particularly, the present invention pertains to the inhibition of complement activation through the inhibition of platelet receptors for thrombin/fibrinogen and to the role of platelet activation in rejection of a transplanted tissue by the body of the recipient of the tissue. As disclosed herein, reagents that inhibit platelet receptors for thrombin/fibrinogen inhibit activation of complement with respect to a transplanted tissue. In a preferred embodiment of the present invention, when both the GPIb and GPIIb/IIIa receptors are inhibited, complement activation product elaboration is greatly retarded. While it is not applicants' desire to be bound by any particular theory of operation, the interaction between platelets and coagulation pathway components are believed to play a role in the initiation of the rejection pathway, which has been established to occur through the activation of complement.

Thus the methods of the present invention utilize reagents that inhibit specific pathways regulating platelet adhesion and/or aggregation. The interactions inhibited by platelet receptor antagonists were not previously known to be involved in the activation of the complement system. Thus, inhibition of this pathway is envisioned, in accordance with the present invention, to prevent events which lead to immediate or later injury to a tissue or organ graft (e.g., hyperacute rejection, delayed xenograft rejection/acute vascular rejection). By blocking a trigger for complement activation, rather than complement activation itself, additional types of cell injury (e.g., endothelial activation) and organ injury (e.g., capillary leak, vessel wall fibroproliferation) can be prevented or attenuated.

Complement activation also has a role during storage of platelets and in diabetes. See Sundsmo, J. S., et al., *Clin Immunol Immunopathol* 35(2):211–25 (May 1985); Bode, A. P., et al., *J. Lab. Clin. Res.* 113(1):94–104 (1989); King, S. B. and Mahmud, E., *Circulation* 2466–2468 (Dec. 21/28, 1999). Thus, the present invention also pertains to the modulation of complement activation in the storage of platelets and in the treatment of diabetes.

A. General Considerations

Numerous studies have contributed to an understanding of the mechanism of platelet aggregation and thrombus formation. Platelets respond to a variety of blood vessel injuries, such as narrowing of the lumen, plaque formation, and the presence of foreign bodies (e.g., catheters) and the like. The response of platelets to these injuries is a sequence of events including platelet adherence and activation, and the release of platelet granular components, including potent cellular mitogenic factors. The activated platelet aggregates induce the formation of fibrin, which further stabilizes the thrombus. Also, an additional platelet receptor has been recently disclosed by Hollopeter, G., et al, "Identification Of The Platelet ADP Receptor Targeted By Antithrombitic Drugs", *Nature* 409:202–207 (Jan. 11, 2001).

Much is now known about mechanisms regulating these responses. Although unstimulated platelets contain receptors for several adhesive proteins including laminin (VLA 2, VLA 6) and collagen (VLA 2, GPIV, others), the initial attachment of platelets to subendothelium is believed to be mainly mediated by the binding of platelet membrane glycoprotein (GP) Ib to the immobilized von Willebrand factor (vWF). Such attachment can also be mediated by collagen or by soluble vWF. Subsequent platelet activation can be initiated by one or more of the known physiological agonists including: ADP, epinephrine, thrombin, collagen, and thromboxane A2.

Thus, one of the major physiologic mechanisms of platelet thrombus formation is Von Willebrand Factor (vWF)-mediated platelet aggregation. The basic interaction of vWF with its major receptor, glycoprotein Ib (GPIb) has been characterized in the art. See e.g. Bockenstedt, et al., *J. Clin. Invest.* 77: 743, (1986).

GPIb is a two-chain molecule having an apparent molecular mass of approximately 160 kDa. GPIb is composed of a heavy (alpha, or GPIb-α) chain, having a molecular mass of approximately 145 kDa linked by disulfide bonds to a light (beta, or GPIb-β) chain, having a molecular mass of approximately 22 kDa. GPIb is an integral membrane protein and both the alpha- and beta-chains described above have transmembrane domains. Proteolysis by an endogenous calcium-dependent platelet protease generates a proteolytic fragment from the amino-terminal portion of GPIb-α, which is known as glycocalicin and which consists of nearly the entire GPIb-α chain, having an approximate molecular mass of 140 kDa. This fragment originates from the extracellular domain of GPIb-α and is water soluble. Thus, it is released after cleavage from the parent molecule.

vWF is a large plasma protein which is synthesized in the endothelial cells which form the inner surface lining of the blood vessel wall, and by megakar ocytes, the precursors of platelets. Large amounts of vWF are found in platelet a-granules, whose contents are released into the blood upon platelet activation. Newly synthesized vWF in endothelial cells may enter the blood via two alternative pathways. Part is secreted constitutively into the blood, mainly as disulfide-linked dimers or small multimers of a 250,000 dalton subunit. Alternatively, part enters secretory organelles called Weibel-Palade bodies. The vWF stored in Weibel-Palade bodies is highly multimeric, ranging in size from that of a dimer to multimers of 50 or more subunits, and can be released from the cells by treatment with secretatogues, such as thrombin. The highly multimeric vWF is the most effective in promoting platelet adhesion.

Mature vWF is a multivalent molecule which has binding sites for several proteins. One of the binding sites recognizes GPIb. Using proteolytic digests this site has been localized to the region between amino acid residues 1449 and 728 of mature vWF. In addition, vWF has at least two collagen binding sites, at least two heparin binding sites, a Factor VIII binding site, and a RGD site which binds to the platelet GP IIb/IIIa receptor.

Platelet aggregation is also mediated by GP IIb-IIIa complex on the platelet membrane surface. GP IIb-IIIa exists on the surface of unstimulated platelets in an inactive form. When platelets are activated by adhesion and the physiological agonists, the GPIIb/IIIa also becomes activated such that it becomes a receptor for fibrinogen (Fg), von Willebrand Factor (vWF), and fibronectin (Fn). See Phillips et al., *Blood* (1988) 71:831–843.

Platelet GPIIb/IIIa is now known to be a member of a superfamily of structurally related adhesive protein receptors known collectively as the "integrns". Like GPIIb/IIIa, all integrins known to date are two subunit molecules with a larger alpha-subunit (e.g., GPIIb) and a smaller beta-subunit (e.g., GPIIIa). There is a high degree of homology between the known sequences of the integrin subunits indicating that the integrins evolved from a common precursor. Integrins function in a variety of cellular adhesions and have been found in leucocytes, endothelial cells, smooth muscle cells and other cells in the vasculature. Because integrins are widely distributed, while GPIIb/IIIa is restricted to platelets, preferred anti-aggregating agents selectively inhibit GPIIb/IIIa as opposed to other integrins.

The complement system is a complex interaction of plasma proteins and membrane cofactors which act in a multi-step, multi-protein cascade sequence in conjunction with other immunological systems of the body to provide immunity from intrusion of foreign cells. Complement proteins represent up to about 10% of globulins in normal serum of man and other vertebrates.

The term "complement" thus refers to the non-specific defense system that is activated by the binding of antibodies to antigens and by this event is directed against specific invaders that have been identified by antibodies. Eleven complement proteins have been characterized in the field and are generally referred to by those having ordinary skill in the art as C1–C9. The complement proteins act generally along a cascade wherein they contribute to (1) recognition (C1); (2) activation (C4, C2, and C3, in that order); and (3) attack (C5–C9). During the attack phase, complement proteins attach to the cell membrane and destroy the victim cell in a process known as complement fixation. The complement system is well known in the art and is more fully described in Fox, *Human Physiology*, William C. Brown Pub., DuBuque, Iowa (1987).

The classic complement pathway involves an initial antibody recognition of, and binding to, an antigenic site (SA) on a target cell. This surface bound antibody subsequently reacts with the first component of complement, C1q, forming a C1-antibody complex with $Ca^{++}$, C1r, and C1s which is proteolytically active. C1s cleaves C2 and C4 into active components, C2a and C4a. The C4b,2a complex is an active protease called C3 convertase, and acts to cleave C3 into C3a and C3b. C3b forms a complex with C4b,2a to produce C4b,2a,3b, which cleaves C5 into C5a and C5b. C5b combines with C6. The C5b,6 complex combines with C7 to form the ternary complex C5b,6,7. The C5b,6,7 complex binds C8 at the surface of the cell, which may develop functional membrane lesions and undergo slow lysis. Upon binding of C9 to the C8 molecules in the C5b,6,7,8 complex, lysis of bacteria and other foreign cells is rapidly accelerated.

In a journal article by Walker, *Int. Archs. Allergy Appl. Immunology* 60:44–491 (1979), the author proposed a role of platelets in complement activation. However, this proposal differs from the present invention since it proposed a secondary, but not a primary role of platelets in complement activation, and it was made in the setting of chemotaxis of neutrophils, and not organ, allo- nor xenotransplantation.

Moreover, the data was developed in a rat-rat model(rat platelets, rat blood). Although the role of complement activation is proposed because of abrogation of chemotaxis by complement inhibition using heat-treatment of plasma, or cobra venom factor, there is no direct, molecular and specific evidence (such as through the use of C deficient animals, or using specific C inhibitors). Indeed, the use by Walker of heat-inactivation to inhibit complement probably also "destroyed" other plasma systems, such as coagulation factors. Furthermore, it is observed in the experiments disclosed in the Examples presented below, that CVF and heat-treatment, used to limit C activation, do indeed lead to complete (CVF) or partial (heat) activation of complement, as can be assessed the measurement of C3a.

Indeed, the methods of the present invention utilize reagents that inhibit the GPIb (preferably GPIb and vWF interaction) and GPIIb/GPIIIa pathways that are involved in regulating platelet adhesion. Prior to the disclosure of the present invention, the interactions inhibited by platelet receptor antagonists were not previously known to be involved in the activation of the complement system, were not known to be involved in the activation of the complement system with respect to a transplanted tissue, and were not known to be involved in the activation of the complement system with respect to a xenograft tissue, such as a pig to human xenograft.

As disclosed herein, reagents that inhibit platelet receptors for thrombin/fibrinogen inhibit activation of complement, and reagents that inhibit platelet receptors for thrombin/fibrinogen inhibit activation of complement with respect to a transplanted tissue, in one embodiment, a xenograft tissue (such as a pig to human xenograft). In a preferred embodiment, when both the GPIb and GPIIb/IIIa receptors are inhibited, complemnent activation product elaboration is greatly retarded. While it is not applicants' desire to be bound by any particular theory of operation, the interaction between platelets and coagulation pathway components are believed to play a role in the initiation of the rejection pathway, which has been established to occur through the activation of complement.

Following long-standing patent law convention, the terms "a" and "an" mean "one or more" when used in this application, including the claims.

B. Therapeutic Methods

In accordance with the present invention a method of modulating complement activation in a warm-blooded vertebrate is provided. The method comprises administering a therapeutically effective amount of a platelet activity modulator to a warm-blooded vertebrate, whereby complement activation is modulated. The term "platelet activity modulator" has been adopted herein for convenience and is meant to refer to any agent that modulates platelet biological activity (e.g. platelet adhesion, activation or aggregation, or other platelet biological activity), the mediators of platelet activity and the pathways associated therewith. Preferred platelet activity modulators inhibit specific pathways regulating platelet adhesion and/or aggregatioen. For example, a "platelet activity modulator" refers to an agent that modulates the biological activity of a platelet aggregation mediator, such as a platelet receptor.

Representative platelet activity modulators thus include anti-thrombin agents (e.g. thrombin inhibitors or antagonists—preferably suitable for local or systemic administration), metabolic inhibitors of thromboxane $A_2$ ($TxA_2$), inhibitors of PGG/H synthase, inhibitors of thromboxane synthase, TxA2 receptor antagonists, serotonin antagonists, and platelet-inhibitory prostanoids and their analogues. Modulation of the additional platelet receptor described by Hollopeter, G., et al. in "Identification Of The Platelet ADP Receptor Targeted By Antithrombitic Drugs", *Nature* 409:202–207 (Jan. 11, 2001) is also provided in accordance with the present invention. The platelet activity modulator preferably comprises a GPIb receptor modulator, a GPIIb/GPIIIa receptor modulator, or a combination of a GPIb receptor modulator and a GPIIb/GPIIIa modulator. As used herein, the terms "modulate", "modulating", and "modulator" are meant to be construed to encompass inhibiting, blocking, promoting, stimulating, agonizing, antagonizing, or otherwise affecting platelet biological activity.

Complement activation has a role in transplant rejection, during storage of platelets and in diabetes. Thus, the present invention also pertains to the modulation of complement activation in treating transplant rejection, in the storage of platelets and in the treatment of diabetes.

In accordance with a preferred embodiment of the present invention, a method of inhibiting complement activation by a transplanted tissue in a warm-blooded vertebrate is provided. The method comprises administering a therapeutically effective amount of a platelet activity modulator to a warm-blooded vertebrate before, during or after a tissue is transplanted to the warm-blooded vertebrate, whereby complement activation by the transplanted tissue is inhibited. Prior to the discoveries of the present invention, it was not known that complement activation, a precursor to transplant rejection, including xenograft rejection (such as a pig to human xenograft), could be modulated by the use of reagents that modulate, and preferably antagonize, platelet biological activity.

In accordance with the present invention, a method of inhibiting rejection of a transplanted tissue in a warm-blooded vertebrate is also provided. The method comprises administering a therapeutically effective amount of a GPIb modulator (preferably a modulator of the GPIb/vWF interaction) and a GPIIb/GPIIIa modulator to a warm-blooded vertebrate before, during or after a tissue is transplanted to the warm-blooded vertebrate, whereby rejection of the transplanted tissue is inhibited. Prior to the discoveries of the present invention, it was not known that transplant rejection could be treated by the use of reagents that modulate, and preferably antagonize, the biological function of GPIb and/or GPIIb/GPIIIa receptor Modulation of the additional platelet receptor described by Hollopeter, G., et al. in "Identification Of The Platelet ADP Receptor Targeted By Antithrombitic Drugs", *Nature* 409:202–207 (Jan. 11, 2001) is also provided in accordance with the present invention.

Any tissue suitable for transplantation falls within the scope of the present invention, including vascularized tissue and non-vascularized, cellular tissue, and including same species tissue or xenographic tissue. Representative vascular tissues include, but are not limited to, heart, lung, liver, kidney, pancreas and combinations thereof. Non-vascular, cellular tissues include, but are not limited to, skin and islets. Implants can thus comprise organs such as liver, kidney, heart and pancreas; body parts such as bone or skeletal matrix; tissue such as bone marrow, skin, intestines, and endocrine glands (e.g. islets); cells, such as cells isolated from organs (e.g. hepatoctes, cardiomyocytes), bone marrow, and progenitor stem cells of various types; and/or artificial organs (e.g. bioreactors, ex vivo organ perfusion). Preferred transplants are the solid, formed and more highly specialized organs such as the liver, kidney, heart or lung.

The present inventive method of inhibiting GPIb/vWF interaction and antagodizing the GPIIb/IIIa platelet receptor to provide for the attenuation of complement activation can thus be employed with respect to species-to-species transplant (an "allograft") as well as xenograft transplant. The present inventive methods are also applicable in ABO-mismatched allograft.

The term "xenograft" is meant to have its art-recognized meaning and to refer to tissue transplant between different but related species. An aspect of the present invention pertains to the observation that the inhibition of platelet activity enhances transplant survival and particularly enhances xenograft survival. The methods of the present invention are thus applicable to human to human transplants and to xenograft transplants from other mammalian species to humans for example, with transplants of primate (e.g. ape and monkey) and porcine (pig) tissue to humans comprising preferred examples. Modulation of the additional platelet receptor described by Hollopeter, G., et al. in "Identification Of The Platelet ADP Receptor Targeted By Antithrombitic Drugs", *Nature* 409:202–207 (Jan. 11, 2001) is also provided in accordance with the present invention.

Thus, in accordance with an alternative embodiment of the present invention a method of enhancing tolerance of a xenograft transplant in a recipient is provided. The method comprises administering a therapeutically effective amount of a GPIb modulator (preferably a modulator of the GPIb/VWF interaction) and a GPIIb/GPIIIa modulator to a recipient before, during or after the recipient receives a xenograft transplant, whereby tolerance of the xenograft transplant is enhanced.

The methods of the present invention can also comprise administration of an agent having activity in the modulation of the complement system itself. See Sims et al., *J. Biol. Chem.* 264(32):19228–19235 and U.S. Pat. No. 5,135,916, incorporated herein by reference in their entirety, for representative complement modulators. Indeed, any art-recognized modulator of complement can be used in the method of the present invention as would be apparent to one of ordinary skill in the art after review of the disclosure herein of the methods of the present invention.

The subject or recipient treated in the present invention in its many embodiments is desirably a human subject, although it is to be understood that the principles of the invention indicate that the invention is effective with respect to all vertebrate species, including mammals, which are intended to be included in the terms "subject" or "recipient". In this context, a mammal is understood to include any mammalian species in which treatment of transplant rejection is desirable, particularly agricultural and domestic mammalian species.

Thus, the methods of the present invention are particularly contemplated to be useful in the treatment of warm-blooded vertebrates. Therefore, the invention concerns mammals and birds.

Contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

The therapeutic compositions used in the method of the present invention are conventionally administered at the site of transplant, or alternatively, intravenously, as by injection of a unit dose, for example. However, as would be apparent to one of ordinary skill in the art, the therapeutic composition may be administered in any suitable manner, including but not limited to, intrasynovial administration, transdermal administration, intramuscular administration, subcutaneous administration, oral administration, intranasal administration or other mucosal route, intraperitoneal administration, intra-cavity administration, and by peristaltic techniques. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration.

It is noted that agents which block platelet function or adhesion prevent the formation of stable clots and thus might be associated with spontaneous bleeding or bleeding from surgical or other sites. While not required, a strategy to manage any such side effects is preferably employed to facilitate safe clinical application and can be adopted by one of ordinary skill in the art without undue experimentation after review of the disclosure presented herein.

C. Modulators of Platelet Activity

Representative platelet activity modulators thus include anti-thrombin agents (e.g. thrombin inhibitors or antagonists—preferably suitable for local or systemic administration), metabolic inhibitors of thromboxane $A_2$ ($TxA_2$), inhibitors of PGG/H synthase, inhibitors of thromboxane synthase, TxA2 receptor antagonists, serotonin antagonists, and platelet-inhibitory prostanoids and their analogues. Modulation of the additional platelet receptor described by Hollopeter, G., et al. in "Identification Of The Platelet ADP Receptor Targeted By Antithrombitic Drugs", Nature 409:202–207 (Jan. 11, 2001) is also provided in accordance with the present invention. The platelet activity modulator preferably comprises a GPIb receptor modulator, a GPIIb/GPIIIa receptor modulator, or a combination of a GPIb receptor modulator and a GPIIb/GPIIIa modulator.

As shown by the present teachings, it is possible to prepare monoclonal antibodies highly selective for immunoreaction with platelet activity mediators, such as thrombin, the GPIb and/or GPIIb/GPIIIa receptor, that are similarly selective for modulation of platelet activity, such as via modulation of thrombin, GPIb and/or GPIIb/GPIIIa receptor function. In addition, peptides and chemical compounds can be designed to be selective for interaction with platelet activity mediators, such as thrombin, GPIb and/or GPIIb/GPIIIa receptor, as described further herein.

Modulators of platelet activity, such as GPIb and/or GPIIb/GPIIIa receptor modulators, are used in the present methods for modulating platelet activity, such as via modulation of GPIb and/or GPIIb/GPIIIa receptor activity in tissues. Thus, as used herein, the terms "modulate", "modulating", and "modulator" are meant to be construed to encompass inhibiting, blocking, promoting, stimulating, agonizing, antagonizing, or otherwise affecting platelet activity, such as via modulation of GPIb receptor activity (preferably GPIb/vWF interaction) and/or GPIIb/GPIIIa receptor activity in tissues. Modulatlion of the additional platelet receptor described by Hollopeter, G., et al. in "Identification of the Platelet ADP Receptor Targeted By Antithrombitic Drugs", Nature 409:202–207 (Jan. 11, 2001) is also provided in accordance with the present invention.

Such modulators can take a variety of forms that include compounds which irnteract with platelet activity mediators, such as the GPIb and/or GPIIb/GPIIIa receptor, in a manner such that functional interactions with natural platelet activity mediator (such as GPIb and/or GPIIb/GPIIIa receptor) ligands are mimicked, stimulated and/or inhibited.

Representative modulators include analogs of a natural ligand binding site on GPIb and/or GPIIb/GPIIIa receptor, mimetics of a natural ligand of GPIb arid/or GPIIb/GPIIIa receptor that mimic the structural region involved in a GPIb and/or GPIIb/GPIIIa receptor-ligand binding interactions, polypeptides having a sequence corresponding to the domain of a natural ligand of GPIb and/or GPIIb/GPIIIa receptor, and antibodies which immunoreact with either an GPIb and/or GPIIb/GPIIIa receptor or a natural ligand, all of which exhibit modulator activity as defined herein.

C.1. Polypeptides

In one embodiment, the invention provides modulators of platelet activity, such as GPIb and/or GPIIb/GPIIIa receptor modulators, in the form of polypeptides. A polypeptide (peptide) modulator can have the sequence characteristics of either a natural ligand of a platelet activity mediator, such as the GPIb and/or GPIIb/GPIIIa receptor, or of a platelet activity mediator itself, such as the GPIb and/or GPIIb/GPIIIa receptor, at the region involved in mediator-ligand interaction. A preferred modulator peptide corresponds in sequence to a natural ligand.

In a preferred embodiment, a polypeptide (peptide) modulator can have the sequence characteristics of either a natural ligand of GPIb and/or GPIIb/GPIIIa receptor or GPIb and/or GPIIb/GPIIIa receptor itself at the region involved in GPIb and/or GPIIb/GPIIIa receptor-ligand interaction. A preferred GPIb and/or GPIIb/GPIIIa receptor modulator peptide corresponds in sequence to a natural ligand.

The term "polypeptide" refers to fusion proteins and polypeptides, recombinant proteins and polypeptides, peptide derivatives, amides, conjugates with proteins, cyclized peptides, polymerized peptides, analogs, fragments, chemically modified peptides, and the like derivatives, as described below.

In one embodiment, an exemplary polypeptide comprises no more than about 100 amino acid residues, preferably no more than about 60 residues, more preferably no more than about 30 residues. Peptides can be linear or cyclic.

It should be understood that a subject polypeptide need not be identical to the amino acid residue sequence of a platelet activity mediator (e.g. GPIb and/or GPIIb/GPIIIa receptor) natural ligand, so long as it includes required binding sequences and is able to function as a modulator of a platelet activity mediator (e.g. GPIb and/or GPIIb/GPIIIa receptor) in an assay, such as is described hereinabove.

A subject polypeptide includes any analog, fragment or chemical derivative of a polypeptide which is a modulator of platelet activity, e.g. a GPIb and/or GPIIb/GPIIIa receptor modulator. Such a polypeptide can be subject to various changes, substitutions, insertions, and deletions where such changes provide for certain advantages in its use. In this regard, a platelet activity modulator polypeptide, e.g. GPIb and/or GPIIb/GPIIIa receptor modulator polypeptide, of this invention corresponds to, rather than is identical to, the sequence of a natural ligand where one or more changes are made and it retains the ability to function as a modulator of platelet activity in one or more of the assays as defined herein. Thus, a polypeptide can be in any of a variety of forms of peptide derivatives, that include amides, conjugates with proteins, cyclized peptides, polymerized peptides, analogs, fragments, chemically modified peptides, and the like derivatives.

The term "analog" includes any polypeptide having an amino acid residue sequence substantially identical to polypeptide modulator as described herein or to a sequence of a natural ligand of a platelet activity mediator (e.g. GPIb and/or GPIIb/GPIIIa receptor) in which one or more residues have been conservatively substituted with a functionally similar residue and which displays platelet activity modulation (e.g. GPIb and/or GPIIb/,GPIIIa receptor modulation) activity as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

The phrase "conservative substitution" also includes the use of a chemically derivatized residue in place of a non-derivatized residue provided that such polypeptide displays the requisite inhibition activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides in accordance with the present invention also include any polypeptide having one or more additions and/or deletions or residues relative to the sequence of a natural ligand of a platelet activity mediator (e.g. GPIb and/or GPIIb/GPIIIa receptor), so long as the requisite activity is maintained. Thus, polypeptides in accordance with the present invention include recombinant and fusion polypeptides.

The term "fragment" refers to any subject polypeptide having an amino acid residue sequence shorter than that of a polypeptide sequence of a polypeptide modulator as described herein, or of a natural ligand of a platelet activity mediator (e.g. GPIb and/or GPIIb/GPIIIa receptor).

When a polypeptide has a sequence that is not identical to the sequence of a polypeptide modulator as described herein or of a platelet activity mediator (e.g. GPIb and/or GPIIb/GPIIIa receptor) natural ligand, it is typically because one or more conservative or non-conservative substitutions have been made, usually no more than about 30 number percent, and preferably no more than 10 number percent of the amino acid residues are substituted. Additional residues may also be added at either terminus of a polypeptide for the purpose of providing a "linker" by which the provided polypeptides can be conveniently affixed to a label or solid matrix, or carrier. Labels, solid matrices and carriers that can be used with the polypesptides of this invention are described hereinbelow.

Amino acid residue linkers are usually at least one residue and can be 40 or more residues, more often 1 to 10 residues, but do not form platelet activity mediator (e.g. GPIb and/or GPIIb/GPIIIa receptor) ligand epitopes. Typical amino acid residues used for linking are tyrosine, cysteine, lysine, glutamic and aspartic acid, or the like. In addition, a subject polypeptide can differ, unless otherwise specified, from the natural sequence of a platelet activity mediator (e.g. GPIb and/or GPIIb/GPIIIa receptor) ligand by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by protease digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

Any peptide of the present invention may be used in the form of a pharmaceutically acceptable salt. Suitable acids which are capable of the peptides with the provided peptides include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the provided peptides include inorganic bases such as sodium hydroxide, ammonium hydroxide, potassium hydroxide and the like; and organic bases such as mono-di- and tri-alkyl and aryl amines (e.g. triethylamine, diisopropyl amine, methyl amine, dimethyl amine and the like), and optionally substituted ethanolamines (e.g. ethanolamine, diethanolamine and the like).

A polypeptide modulator, also referred to herein as a subject polypeptide, can be synthesized by any of the techniques that are known to those skilled in the polypeptide art, including recombinant DNA techniques and techniques associated with the preparation of fusion polypeptides. Thus, peptides or their derivatives can be produced recombinantly using methods and techniques well known to those in the art, such as are disclosed in U.S. Pat. No. 5,135,916, herein incorporated by reference in its entirety.

Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, *Adv Enzymol*, 32:221–96, 1969; Fields et al., *Int. J. Peptide Protein Res.*, 35:161–214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In, general, the solid-phase synthesis methods provided comprise the sequential addition of one or more amino acid residues or suitably protected amino acid residues to a growing peptide chain. Normally, either the amino or carboxyl group of the first amino acid residue is protected by a suitable, selectively removable protecting group. Preferably a different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above may be reacted to form their corresponding cyclic peptides. An exemplary method for cyclizing peptides is described by Zimmer et al., *Peptides* 1992, pp. 393–394, ESCOM Science Publishers, B. V., 1993. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

C.2. Monoclonal Antibodies

The present invention describes, in one embodiment, modulators of platelet activity in the form of monoclonal antibodies which immunoreact with a platelet activity mediator (e.g. GPIb and/or GPIIb/GPIIIa receptor) and bind the platelet activity mediator to modulate platelet activity, such as via modulation of GPIb and/or GPIIb/GPIIIa receptor biological activity as described herein. The invention also describes cell lines which produce the antibodies, methods for producing the cell lines, and methods for producing the monoclonal antibodies.

A monoclonal antibody of this invention comprises antibody molecules that 1) immunoreact with an isolated platelet activity mediator (e.g. GPIb and/or GPIIb/GPIIIa receptor), and 2) bind to a platelet activity mediator (e.g. GPIb and/or GPIIb/GPIIIa receptor) to modulate its biological function.

The term "antibody or antibody molecule" in the various grammatical forms are used herein as a collective noun that refers to a population of immunoglobulin molecules and/or immunologically active portions of immunoglobulin molecules, i.e., molecules that contain an antibody combining site or paratope. An "antibody combining site" is that structural portion of an antibody molecule comprised of heavy and light chain variable and hypervariable regions that specifically binds antigen.

Exemplary antibodies for use in the present invention are intact immunoglobulin molecules, substantially intact immunoglobulin molecules, single chain immunoglobulins or antibodies, those portions of an immunoglobulin molecule that contain the paratope, including those portions known in the art as Fab, Fab', F(ab')2 and F(v), and also referred to as antibody fragments. For example, use of scFv antibody fragments against GP IIb/IIIa can be employed in accordance with the present invention.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each imrmunospecific for a different epitope, e.g., a bispecific monoclonal antibody.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature* 256:495–497 (1975), which description is incorporated by reference. Additional methods are described by Zola, *Monoclonal Antibodies: a Manual of Techniques*, CRC Press, Inc. (1987). The hybridoma supernates so prepared can be screened for the presence of antibody molecules that immunoreact with a platelet activity mediator (e.g. GPIb and/or GPIIb/GPIIIa receptor) and for inhibition of a platelet activity mediator (e.g. GPIb and/or GPIIb/GPIIIa receptor) biological functions.

Briefly, to form the hybridoma from which the monoclonal antibody composition is produced, a myeloma or other self-perpetuating cell line is fused with lymphocytes obtained from the spleen of a mammal hyperimmunized with a source of a platelet activity mediator (e.g. GPIb and/or GPIIb/GPIIIa receptor). It is preferred that the myeloma cell line used to prepare a hybridoma be from the same species as the lymphocytes. Typically, a mouse of the strain 129 GlX+ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the ATCC, Manassas, Va., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using an ELISA, for examples.

A provided monoclonal antibody can also be produced by initiating a monoclonal hybridoma culture comprising a nutrient medium containing a hybridorna that secretes antibody molecules of the appropriate specificity. The culture is maintained under conditions and for a time period sufficient for the hybridoma to secrete the antibody molecules into the medium. The antibody-containing medium is then collected. The antibody molecules can then be further isolated by well known techniques. Media useful for the preparation of these compositions are both well known in the art and commercially available and include synthetic culture media, inbred mice and the like. An exemplary synthetic medium is Dulbecco's minimal essential medium(DMEM-Dulbecco et al., *Virol* 8:396 (1959)) supplemented with 4.5 gm/1 glucose, 20 mM glutamine, and 20% fetal calf serum. An exemplary inbred mouse strain is the Balb/C.

Other methods of producing a monoclonal antibody, a hybridoma cell, or a hybridoma cell culture are also well known. See, for example, the method of isolating monoclonal antibodies from an immunological repertoire as described by Sastry, et al., *Proc Natl Acad Sci USA* 86:5728–5732 (1989); and Huse et al., *Science* 246:1275–1281 (1989).

It is also possible to determine, without undue experimentation, if a monoclonal antibody has the same (i.e., equivalent) specificity (immunoreaction characteristics) as a monoclonal antibody of this invention by ascertaining whether the former prevents the latter from binding to a preselected target molecule (e.g. GPIb or GPIIb/GPIIIa receptor). If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the target molecule with which it is normally reactive, and then add the monoclonal antibody being tested to determine if the monoclonal antibody being tested is inhibited in its ability to bind the target molecule (e.g. GPIb or GPIIb/GPIIIa receptor). If the monoclon, al antibody being tested is inhibited then, in all likelihood, it has the same, or, functionally equivalent, epitopic specificity as the monoclonal antibody of the invention.

An additional way to determine whether a monoclonal antibody has the specificity of a monoclonal antibody of the invention is to determine the amino acid residue sequence of the CDR regions of the antibodies in question. "CDRs" (complementarity determining regions) mean the three sub-regions of the light or heavy chain variable regions which have hypervariable sequences and form loop structures that are primarily responsible for making direct contact with antigen. Antibody molecules having identical, or functionally equivalent, amino acid residue sequences in their CuR regions have the same binding specificity. Methods for sequencing polypeptides are well known in the art.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin that comprises the antibody, and in part by the light chain variable region amino acid residue sequence. Use of the terms "having the binding specificity of" or "having the binding preference of" indicates that equivalent monoclonal antibodies exhibit the same or similar immunoreaction (binding) characteristics and compete for binding to a preselected target molecule.

Humanized monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention. Thus, the invention provides, in one embodiment, a monoclonal antibody of this invention that is humanized by grafting to introduce components of the human immune system without substantially interfering with the ability of the antibody to bind antigen. Alternatively, "fully" human antibodies can be produced by immunizing transgenic mice carrying human Ig-genes. See Bruggeman, N. and Neuberger, M. S., *Immunol. Today* 17(8):391–7 (August 1996); Longberg, N. and Huszar, D., *Int. Rev. Immunol.* 13(1):65–93 (1995); Jakobvits, A., *Curr. Opin. Biotechnol.* 6(5):561–6; Bruggeman, N. and Neuberger, M., *Nature* 386(6620):25–6 (March 1997); Nguyen, H., et al., *Microbiol. Immunol.* 41(12):901–7 (1997).

The use of a molecular cloning approach to generate antibodies, particularly monoclonal antibodies, and more particularly single chain monoclonal antibodies, is also provided. The production of single chain antibodies has been described in the art, see e.g., U.S. Pat. No. 5,260,203, the contents of which are herein incorporated by reference. For this, combinatorial immunoglobulin phagemid libraries are prepared from RNA isolated from the spleen of the immunized animal, and phagemids expressing appropriate antibodies are selected by panning on endothelial tissue. The advantages of this approach over conventional hybridoma techniques are that approximately $10^4$ times as many antibodies can be produced and screened in a single round, and that new specificities are generated by H and L chain combination in a single chain, which further increase's the chance of finding appropriate antibodies. Thus, an antibody of the present invention, or a "derivative" of an antibody of the present invention pertains to a single polypeptide chain binding molecule which has binding specificity and affinity substantially similar to the binding specificity and affinity of the light and heavy chain aggregate variable region of an antibody described herein.

C3. Other Modulators

Given the disclosure of the platelet activity in tissues herein, it is also provided that other chemical compounds may be used to modulate a platelet activity (e.g. GPIb and/or GPIIb/GPIIIa receptor activity) in tissues in accordance with the methods of the present invention. Particularly provided chemical entities do not naturally occur in any cell of a lower eucaryotic organism such as yeast. More particularly, provided chemical entities do not naturally occur in any cell, whether of a multicellular or a unicellular organism. Even more particularly, the provided chemical entity is not a naturally occurring molecule, e.g. it is a chemically synthesized entity.

Such modulators can take a variety of forms that include compounds which interact with a platelet activity mediator (e.g. GPIb and/or GPIIb/GPIIIa receptor) in a manner such that functional interactions between the platelet activity mediator and an endogenous ligand are mimicked, stimulated and/or inhibited. Exemplary modulators include analogs of a binding site on a platelet activity mediator or on a platelet activity mediator ligand and mimetics of a structural region involved in platelet activity mediator binding interactions with native ligands. Many such chemical modulators are known in the art, and representative chemical modulators are set forth herein below and in the Examples.

C.4. Representative Modulators

A representative GPIb modulator is aurin tricarboxylic acid (ATA). ATA is described in the Examples, in U.S. Pat. No. 4,880,788 and in Girma et al., (1992), incorporated herein by reference in their entirety.

Representative polypeptide modulators of GPIb and of GPIb/vWF interaction are disclosed in the following patents and patent publications: JP 8034800; WO 92/08472; U.S. Pat. No. 6,008,193; U.S. Pat. No. 5,900,476; U.S. Pat. No. 5,849,702; U.S. Pat. No. 5,849,536; U.S. Pat. No. 5,837,488; and U.S. Pat. No. 5,336,667, the entire contents of each of which are herein incorporated by reference.

Representative GPIIb/GPIIIa receptor modulators that can be used in the methods of the present invention include the 7E3 antibody—generic name labciximab, sold under the trade name RHEOPRO™; snake venom proteins, such as INTEGRELIN™ (COR Therapeutics of South San Francisco, Calif.); and the non-peptide compounds, ticlopidine, Ro44-9883 and RO43-8857 (F. Hoffman-LaRoche AG of Basel, Switzerland), MK-383 (Merck & Co., Inc., of Rahway, N.J.), SC54684 (G. D. Searle & Co. of Chicago, Ill.), GR144053 (Glaxo-Wellcome Inc. of Research Triangle Park, N.C.), and DMP738 (The DuPont Merck Pharmaceutical Company of Wilmington, Del.). See also Nurden, A. T., et al., *Arterioscler. Thromb. Vasc. Biol.* 2835–2840 (December 1999); Coller et al., *Thrombin and Haemostasis* 74(1):302–308 (1995), herein incorporated by reference in their entirety.

Additional representative GPIIb/GPIIIa receptor modulators that can be used in the methods of the present invention are disclosed in the following U.S. patents, the entire contents of each of which also are herein incorporated by reference:

| | |
|---|---|
| U.S. Pat. No. 5,976,532 | Method of anti-thrombotic therapy using anti-GPIIb/IIIa antibodies or fragments thereof, including c7E3 |
| U.S. Pat. No. 5,858,972 | Anti-thrombotic agents and methods of use |
| U.S. Pat. No. 5,731,324 | Glycoprotein IIb/IIIa antagonists |
| U.S. Pat. No. 5,705,890 | Tricyclic inhibitors of the GPIIb/IIIa receptor |
| U.S. Pat. No. 5,618,843 | Glycoprotein IIb/IIIa antagonists |

Additional platelet activity modulators that can be used in the methods of the present invention are disclosed in the following U.S. patents, the entire contents of each of which also are herein incorporated by reference:

| | |
|---|---|
| U.S. Pat. No. 5,973,003 | Substituted β-amino acid derivatives useful as platelet aggregation inhibitors |
| U.S. Pat. No. 5,886,208 | Substituted β-amino acid derivatives useful as platelet aggregation inhibitors |
| U.S. Pat. No. 5,811,398 | Platelet aggregation inhibitors containing C-terminal aminergic side chain amino acid residues |
| U.S. Pat. No. 5,798,370 | Platelet aggregation inhibitors |
| U.S. Pat. No. 5,721,366 | Platelet aggregation inhibitors |
| U.S. Pat. No. 5,703,125 | Substituted β-amino acid derivatives useful as platelet aggregation inhibitors |
| U.S. Pat. No. 5,674,894 | Amidine derivatives useful as platelet aggregation inhibitors and vasoditators |
| U.S. Pat. No. 5,652,363 | Pyrido-1,4-oxazinylalkyl-benzamide derivatives |
| U.S. Pat. No. 5,646,183 | Phenyl amidine alkanoic acids useful as platelet aggregation inhibitors |
| U.S. Pat. No. 5,612,355 | Phenyl amidine lactones useful as platelet aggregation inhibitors |
| U.S. Pat. No. 5,602,155 | Platelet aggregation inhibitors |
| U.S. Pat. No. 5,552,431 | Peptide mimetic compounds useful as platelet aggregation inhibitors |
| U.S. Pat. No. 5,543,425 | Method of inhibiting platelet aggregation using phenyl amidine thio derivatives |
| U.S. Pat. No. 5,504,106 | Phenyl amidine alkanoic acids and lactones useful as platelet aggregation inhibitors |
| U.S. Pat. No. 5,489,594 | Platelet aggregation inhibitors |
| U.S. Pat. No. 5,481,021 | Phenyl amidines derivatives useful as platelet aggregation inhibitors |
| U.S. Pat. No. 5,441,974 | Phenyl amidines lactones useful as platelet aggregation inhibitors |
| U.S. Pat. No. 5,430,043 | Platelet aggregation inhibitors |
| U.S. Pat. No. 5,424,334 | Peptide mimetic compounds useful as platelet aggregation inhibitors |
| U.S. Pat. No. 5,409,939 | Phenyl amidine thio derivatives useful as platelet aggregation inhibitors |
| U.S. Pat. No. 5,378,727 | Substituted bicyclic heterocyclic compounds useful as platelet aggregation inhibitors |
| U.S. Pat. No. 5,360,907 | Pyrrolo[3,2-B]pyridinylalkyl benzamide derivatives |
| U.S. Pat. No. 5,354,738 | Platelet aggregation inhibitors |
| U.S. Pat. No. 5,344,957 | Substituted β-amino acid derivatives useful as platelet aggregation inhibitors |
| U.S. Pat. No. 5,344,837 | Platelet aggregation inhibitors |
| U.S. Pat. No. 5,302,601 | 5-substituted imidazo[4,5-c]pyridines |
| U.S. Pat. No. 5,264,457 | Phenyl amidines sulfonamides useful as platelet aggregation inhibitors |
| U.S. Pat. No. 5,262,426 | N,N'-cycloalkyl/alkyl carboxamide 4H-imidazo-[4,5-b]pyridine compounds as PAF antagonists |
| U.S. Pat. No. 5,254,573 | Substituted heterocyclic derivatives useful as platelet aggregation inhibitors |
| U.S. Pat. No. 5,227,384 | 5-substituted [4,5-c] imidazopyridines and pharmaceutical use thereof |
| U.S. Pat. No. 5,223,539 | N,N-Di-alkyl(phenoxy)benzamide derivatives |
| U.S. Pat. No. 5,220,050 | Peptide mimetic compounds useful as platelet aggregation inhibitors |
| U.S. Pat. No. 5,208,242 | 5-substituted-4-phenyl-5H-imidazo [4,5-c]pyridine derivatives |
| U.S. Pat. No. 5,091,396 | Pyridyl peptide mimetic compounds which are useful platelet-aggregation inhibitors |
| U.S. Pat. No. 5,053,393 | Novel platelet-aggregation inhibitor |
| U.S. Pat. No. 5,037,808 | Indolyl platelet-aggregation inhibitors |
| U.S. Pat. No. 5,019,581 | 5-substituted (4,5-c) imidazopyridine compounds which have useful platelet activating factor antagonistic activity |
| U.S. Pat. No. 4,990,518 | Pharmacologically active heteroaryl substituted imidazo (4,5-c) pyridines |
| U.S. Pat. No. 4,988,707 | Pharmacologically active phenylalkanoyl substituted imidazo (4,5-C) pyridines |
| U.S. Pat. No. 4,962,106 | Imidazopyridine derivatives |
| U.S. Pat. No. 4,914,108 | 5-substituted(4,5-c)imidazopyridine compounds which have useful platelet activating factor antagonistic activity |
| U.S. Pat. No. 4,857,508 | Novel platelet-aggregation inhibitor peptide derivatives |
| U.S. Pat. No. 4,758,573 | Heterocyclic group-containing compounds |
| U.S. Pat. No. 4,719,220 | 15(R)-5-fluoroprostacycfins, pharmaceutical compositions and anti-thrombotic methods of use thereof |

| | |
|---|---|
| U.S. Pat. No. 4,616,034 | 15(R)-5-fluoroprostacyclins, pharmaceutical compositions and anti-thrombotic method of use thereof |

Representative anti-thrombin agents include heparin, hirudin (a 65-amino acid polypeptide available under the trade name HIRUGEN™), bifunctional antithrombin peptide (BAP—available under the registered trademark HIRULOG® from Biogen, Inc. of Cambridge, Mass.), D-FRBOH, D-FPRCH$_2$Cl, D-FG-boroArg, D-FPRH, D-Phe-Pro-Arg, D-MePhe-Pro-Arg-H, arginine, borogarginine, benzamidine and benzamindine type, and argatroban (argipidine or MD-805), as well as compounds disclosed in U.S. Pat. No. 6,017,934, herein incorporated by reference.

Examples of TXA$_2$ modulators include, but are not limited to, TXA$_2$ receptoriantagonists and TXA$_2$ synthase inhibitors. Exemplary thromboxane A$_2$ receptor antagonists include, but are not limited to, heterocyclic amido prostaglandin analogs such as those described in U.S. Pat. Nos. 5,158,9617; 5,238,951; 5,550,248; 5,312,818; 5,126,370; 5,290,799, the entire contents of each of which are herein incorporated by reference.

Additional thromboxane A$_2$ receptor antagonists and thromboxane A$_2$ synthase inhibitors provided for use in the methods of the present invention are disclosed in the following U.S. patents, the contents of each of which also are herein incorporated by reference: U.S. Pat. No. 5,410,064 (1,3-dioxane alkenoic acid derivatives); U.S. Pat. No. 5,356,921 (3- and 4-(1H-imidazol-1-yl)phenol compounds having TXA$_2$ synthase inhibitor activity); U.S. Pat. No. 5,283,254 (2-(imidazol-1-yl)-2-benzylethyidiene-aminoxyalkanoic acid derivatives); U.S. Pat. No. 5,744,488 (indole derivatives TXA$_2$ antagonists); U.S. Pat. No. 5,401,849 (4-pyridyl-1,3-dioxane derivatives); U.S. Pat. No. 5,516,791 (7-[carboxyakyl or alkenyl]-6-[alkyl or alkenyl]-3-oxo-2,4-dioxobicyclo-[3.2.1]octane and derivatives thereof); and U.S. Pat. No. 5,741,812 (thromboxane ligands).

Indeed, any art-recognized modulator of platelet activity, including any art-recognized GPIb and/or GPIIb/GPIIIa receptor-modulators can be used in the method of the present invention as would be apparent to one of ordinary skill in the art after review of the disclosure herein of the methods of the present invention.

D. Pharmaceutical Compositions

The present invention provides therapeutic compositions useful for practicing the therapeutic methods described herein. Therapeutic compositions of the present invention contain a physiologically tolerable carrier together with a platelet activity modulator (e.g. a GPIb and/or GPIIb/GPIIIa receptor modulator) as described herein, dissolved or dispersed therein as an active ingredient. In a preferred embodiment, the therapeutic platelet activity modulator composition is not immunogenic when administered to a subject for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a patient without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions; however, lisolid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharm aceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. liquid compositions can also contain liquid phases in addition to and to the exclusion of water. Exemplary of such additional liquid phases are glycerin, vegetable oils such as cottonseed oil, and water-oil emulsions.

A therapeutic composition contains a platelet activity (e.g. GPIb and/or GPIIb/GPIIIa receptor)-modulating amount of a modulator of platelet activity in accordance with the present invention, typically formulated to contain an amount of at least 0.1 weight percent of modulator per weight of total therapeutic composition. A weight percent is a ratio by weight of modulator to total composition. Thus, for example, 0.1 weight percent is 0.1 grams of inhibitor per 100 grams of total composition.

Suitable pharmaceutical compositions can optionally include buffers such as phosphate buffered saline (PBS), or additional additives such as pharmaceutical excipients, stabilizing agents such as BSA or HSA, or salts such as sodium chloride. For parenteral administration it is generally desirable to further render such compositions pharmaceutically acceptable by insuring their sterility, non-immunogenicity and non-pyrogenicity. Such techniques are generally well known in the art as exemplified by *Remington's Pharmaceutical Sciences*, 16th Ed. Mack Publishing Company (1980), incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

E. Dosage Information

Actual dosage levels of active ingredients in the pharmaceutical compositions of this invention may be varied so as to administer an amount of the active compound(s) that is effective to achieve the desired therapeutic response for a particular subject. The selected dosage level will depend upon the activity of the particular compound, the route of administration, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved.

If desired, the effective daily dose may be divided into multiple doses for purposes of administration, e.g., two to four separate doses per day. It will be understood, however, that the specific dose level for any particular subject will depend upon a variety of factors including the body weight, general health, diet, time and route of administration, combination with other drugs and the severity of the particular disease being treated.

The dosage ranges for the administration of the a modulator of platelet activity (e.g. GPIb and/or GPIIb/GPIIIa receptor modulator) depend upon the form of the modulator, and its potency, as described further herein, and are amounts large enough to produce the desired effect in which transplant rejection through complement activation and related effects of complement activation as a precursor to transplant rejection are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can also be adjusted by the individual physician in the event of any complication.

The therapeutic compositions can be administered as a unit dose. The term "unit dose" when used in reference to a therapeutic composition employed in the method of the present invention refers to physically discrete units suitable as unitary dosage for the subject, each unit containing a predetermined quantity of active material calculated to produce the desired therapeutic effect in association with the required diluent; i.e., carrier or vehicle.

The compositions are administered in a manner compatible with the dosage formulation, and in a therapeutically effective amount. The quantity to be administered depends on the subject to be treated, capacity of the subjects system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies can also be administered.

A therapeutically effective amount is an amount of a modulator sufficient to produce a measurable modulation of platelet activity (e.g. GPIb and/or GPIb/GPIIIa receptor activity) in a subject being treated, i.e., a platelet activity-modulating amount. Modulation of platelet activity (e.g. GPIb and/or GPIIb/GPIIIa receptor activity) can be measured by analyzing complement activation as disclosed in the Examples, by in situ immunohistochemistry or by other methods known to one skilled in the art.

Insofar as a modulator can take the form of a platelet activity mediator (e.g. GPIb and/or GPIIb/GPIIIa receptor) ligand mimetic, and an anti-platelet activity mediator (e.g. GPIb and/or GPIIb/GPIIIa receptor) monoclonal antibody, or fragment thereof, it is to be appreciated that the potency, and therefore an expression of a "therapeutically effective" amount can vary. However, as shown by the Examples presented below, one skilled in the art can readily assess the potency of a modulator of a platelet activity mediator employed in the methods of the present invention.

A preferred modulator has the ability to substantially bind to a platelet activity mediator (e.g. GPIb and/or GPIIb/GPIIIa receptor) in solution at modulator concentrations of less than one (1) micro molar ($\mu$M), preferably less than 0.1 $\mu$M, and more preferably less than 0.01 $\mu$M. By "substantially" is meant that at least a 50 percent reduction in platelet activity mediator (e.g. GPIb and/or GPIIb/GPIIIa receptor) biological activity is observed by modulation in the presence of the modulator of the platelet activity mediator, and at 50% reduction is referred to herein as an IC50 value.

In one embodiment, the therapeutically effective amount of a GPIb modulator and a therapeutically effective amount of the GPIIb/GPIIIa modulator can respectively range from about 0.01 mg to about 10,000 mg per day. Alternatively, the therapeutically effective amount of GPIb modulator and the therapeutically effective amount of the GPIIb/GPIIIa modulator can respectively range from about 0.1 mg to about 1,000 mg per day. Alternatively, the therapeutically effective amount of GPIb modulator and the therapeutically effective amount of the GPIIb/GPIIIa modulator can respectively range from about 1 mg to about 300 mg per day. In a preferred embodiment, the therapeutically effective amount of GPIb modulator and the therapeutically effective amount of the GPIIb/GPIIIa modulator can respectively range from about 15 mg per kg body weight per day to about 35 mg per kg body weight per day.

In another embodiment, a therapeutically effective amount of a modulator of a platelet activity mediator (e.g. GPIb and/or GPIIb/GPIIIa receptor) of this invention in the form of a monoclonal antibody, or fragment thereof, is typically an amount such that when administered in a physic logically tolerable composition is sufficient to achieve a plasma concentration of from about 0.01 microgram (ug) per milliliter (mL) to about 100 ug/mL, preferably from about 1 ug/mL to about 5 ug/mL, and usually about 5 ug/mL. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

In another embodiment, a therapeutically effective amount of a modulator of a platelet activity mediator (e.g. GPIb and/or GPIIb/GPIIIa receptor) of this invention in the form of a polypeptide is typically an amount of polypeptide such that when administered in a physiologically tolerable composition is sufficient to achieve a plasma concentration of from about 0.001 microgram ($\mu$g) per milliliter (mL) to about 10 $\mu$g/mL, preferably from about 0.05 $\mu$g/mL to about 1.0 ug/mL. Based on a polypeptide having a mass of about 15,000 grams per mole (i.e. 15,000 Da), the preferred plasma concentration in molarity is from about 0.0001 micro molar ($\mu$M) to about 1 milli molar (mM). Stated differently, the dosage per body weight can vary from about 0.01 mg/kg to about 30 mg/kg, and preferably from about 0.05 mg/kg to about 20 mg/kg, in one or more dose administrations daily, for one or several days.

The chemical modulators, monoclonal antibodies or polypeptides of the invention can be administered parenterally by injection or by gradual infusion over time. Although the tissue to be treated can typically be accessed in the body by systemic administration and therefore treated by intravenous administration of therapeutic compositions, delivery of a therapeutic composition at the site of transplant can also be used in accordance with the methods of the present invention. Additionally, therapeutic compositions employed in the methods of the present invention can be administered orally, intravenously, intraperitoneally, intramuscularly, subcutaneously, intra-cavity, transdermally, and can be delivered by peristaltic techniques.

F. Donor Animal Sources of Xenograft Tissues

In accordance with the present invention that donor animals can be prepared wherein certain platelet activity pathway components are "knocked out" or otherwise inactivated. Such animals then provide xenograft tissue or organs for transplant to humans, for example, which take advantage of the observation in accordance with the present invention that platelet activity inhibition enhances xenograft survival. Donor animals can be prepared using transgenic and/or transduction approaches, to thereby faciliate the use of fusion/recombinant proteins/peptides in addition to synthetic peptides or purified salts administered systematically, and use of scFv antibody fragments (e.g. against GPIIb/GPIIIa) in the treatment of xenograft rejection.

For example, a pig that is deficient in von Willebrand's Factor (vWF) or is (vWF -, -) can be prepared for use as a donor. Tissue or organs from such a donor animal are transplanted in conjunction with the administration of a GPIIb/IIIa modulator to thereby facilitate survival of the xenograft transplanted from such an animal in accordance with the methods of the present invention. In a preferred embodiment, a donor animal in accordance with the present invention is a transgenic animal. Techniques for the preparation of transgenic animals, including "knock out" animals, are known in the art. Representative techniques are described in U.S. Pat. No. 5,1489,742 (transgenic rats); U.S. Pat. Nos. 4,736,866, 5,550,316, 5,614,396, 5,625,125 and U.S. Pat. No. 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), the entire contents of each of which are herein incorporated by reference.

Briefly, a method by which the expression of specific genes can be inhibited in a transgenic animal is by genetic manipulations referred to in the art as "gene disruption" or "gene knockout". Gene knockout is a method of genetic manipulation via homologous recombination that has long been carried out in microorganisms, but has only been practiced in mammalian cells within the past decade. These techniques allow for the use of specially designed DNA molecules (gene knockout constructions) to achieve targeted inactivation (knockout) of a particular gene upon introduction of the construction into a cell. The practice of mammalian gene knockout, including the design of gene knockout constructions and the detection and selection of successfully altered mammalian cells, is discussed in numerous publications, including Thomas et al., 1986; Thomas et al., 1987; Jasin and Berg, 1988; Mansour et al. 1988; Brinster et al., 1989; Capecchi 1989; Frohman and Martin, 1989; Hasty et al., 1991; Jeannotte et al., 1991; and Mortensen et al., 1992.

Gene knockouts and gene replacements can be achieved in mammalian zygotes through microinjection techniques well known in the art (Brinster et al., 1989). The introduction of the DNA constructions used to effect gene knockouts into cultured cells is a more common route to the production of knockout cells, tissues, and organs. In those cases where knockout tissues or organs are desired, cultured embryonic stem cells provide a means to introduce the DNA constructions into cells in culture and to generate transgenic animals derived from such engineered cells. Such animals can also be obtained from knockout transgenic zygotes obtained by microinjection.

Thus, transgenic animals can be prepared using techniques known in the art. These techniques include, but are not limited to, microinjection, e.g., of pronuclei, electroporation of ova or zygotes, nuclear transplantation, and/or the stable transfection or transduction of embryonic stem cells.

The most well known method for making transgenic animals is that used to produce transgenic mice by superovulation of a donor female, surgical removal of the egg, injection of the transgene transcription unit into the pronuclei of the embryo, and introduction of the transgenic embryo into the reproductive tract of a pseudopregnant host mother, usually of the same species. See U.S. Pat. No. 4,873,191; Brinster et al., 1985; Hogan et al., 1986; Robertson 1987; Pedersen, et al., 1990.

The use of this method to make transgenic livestock is also widely practiced by those of skill in the art. As an example, transgenic swine are routinely produced by the microinjection of nucleic acid molecules into pig embryos. See, for example, PCT Publication No. WO 92/11757. In brief, this procedure may, for example, be performed as follows. First, the nucleic acid molecules are gel isolated and extensively purified, for example, through an ELUTIP® column (Schleicher & Schuell, Keene, N.H.), dialyzed against pyrogen free injection buffer (10 nM Tris, pH7.4+0.1 mM EDTA in pyrogen free water), and used for embryo injection.

Embryos are recovered from the oviduct of a hormonally synchronized, ovulation induced sow, preferably at the pronuclear stage. They are placed into a 1.5 ml microfuge tube containing approximately 0.5 ml of embryo transfer media (phosphate buffered saline with 10% fetal calf serum). These are centrifuged for 12 minutes at 16,000×g in a microcentrifuge. Embryos are removed from the microfuge tube with a drawn and polished Pasteur pipette and placed into a 35 mm petri dish for examination. If the cytoplasm is still opaque with lipid such that the pronuclei are not clearly visible, the embryos are centrifuged again for an additional 15 minutes.

Embryos to be microinjected are placed into a drop of media (approximately 100 $\mu$l) in the center of the lid of a 100 mm petri dish. Silicone oil is used to cover this drop and to fill the lid to prevent the medium from evaporating. The petri dish lid containing the embryos is set onto an inverted microscope equipped with both a heated stage (37.5°–38° C.) and Hoffman modulation contrast optics (200× final magnification). A finely drawn and polished micropipette is used to stabilize the embryos while about 1–2 picoliters of injection buffer containing approximately 200–500 copies of the purified transgene transcription unit is delivered into the nucleus, preferably the male pronucleus, with another finely drawn and polished micropipette. Embryos surviving the microinjection process as judged by morphological observation are loaded into a polypropylene tube (2 mm ID) for transfer into the recipient pseudopregnant sow.

Offspring are tested for the presence of the transgene by isolating genomic DNA, e.g., from tissue removed from the tail of each piglet, and subjecting about 5 micrograms of this genomic DNA to nucleic acid hybridization analysis with a transgene specific probe.

Another commonly used technique for generating transgenic animals involves the genetic manipulation of embryonic stem cells (ES cells) as described in PCT Patent Publication No. WO 93/02188 and Robertson, 1987. In accordance with this technique, ES cells are grown as described in, for example, Robertson, 1987, and in U.S. Pat. No. 5,166,065. Genetic material is introduced into the embryonic stem cells by, for example, electroporation according, for example, to the method of McMahon, et al., 1990, or by transduction with a retroviral vector according, for example, to the method of Robertson, et al., 1986, or by any of the various techniques described by Lovell-Badge, 1987.

Chimeric animals are generated as described, for example, in Bradley, 1987. Briefly, genetically modified ES cells are introduced into blastocysts and the modified blastocysts are then implanted in pseudo-pregnant female animals. Chimeras are selected from the offspring, for example by the observation of mosaic coat coloration resulting from differences in the strain used to prepare the ES cells and the strain used to prepare the blastocysts, and are bred to produce non-chimeric transgenic animals. Other methods for the production of transgenic animals are disclosed in U.S. Pat. No. 5,880,327; U.S. Pat. No. 5,032,407; and PCT Publication No. WO90/08832. The practice of gene knockout in embryonic stem cells, and the generation of engineered animals from such cells, is discussed in numerous publications, including PCT Patent Publication No. WO 93/02188.

A cDNA for vWF is available from the American Type Culture Collection, Manassas, Va. U. S. Pat. Nos. 5,492,809 and 5,298,239 (herein incorporated by reference in their entirety) disclose nucleic acid molecules including mutations rendering platelet glycoprotein Ib-α less reactive with vWF. Preferably, the mutation is in the leucine rich region of GPIb-α, such as the substitution of phenylalanine for leucine at residue 57. Such nucleic acid molecules can be used in the preparation of a transgenic donorianimal in accordance with the present invention.

Other methods for the production of donor animals include the use of nuclear transfer to remove expression of a specific gene (e.g. a vWF deficient pig line) and the transduction of tissue for transplantation using viral vectors (adeno, AAV, lentiviruses, and the like) and other vectors. See Campbell, K. H., *Semin. Cell Dev. Biol.* 10(3):245–52 (June 1999); Schnieke, A. E., et al., *Science* 278(5346):2130–3 (Dec. 19, 1997); Cibelli, J. B., et al., *Science* 280(5367):1256–8 (May 22, 1998); PCT Publication No. WO 96/38543, herein incorporated by reference in their entirety. Additionally, in a transgenic pig donor animal for example, expression of a transgene can be dependent on endothelial/target cell activation. Thus, donor animals can be prepared using transgenic and/or transduction approaches, to thereby faciliate, the use of fusion/recombinant proteins/peptides in addition to synthetic peptides or purified salts administered systematically, and use of scFv antibody fragments (e.g. against GPIIb/GPIIIa) in the treatment of xenograft rejection.

EXAMPLES

The following Examples have been included to illustrate preferred modes of the invention. Certain aspects of the following Examples are described in terms of techniques and procedures found or provided by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Examples 1–3

In Situ Ex Vivo Isolated Lung Perfusion Model
Materials and Methods Employed In Examples 1–3

In accordance with the present invention, Examples 1–3 presented herein below in Table 1 pertain to and analyze the role of platelet activation and aggregation in hyperacute rejection of a pig lung by human blood. Outbreak piglets (4–6 kg) were used in an established in situ ex vivo isolated lung perfusion model. Piglet lungs were perfused with unmodified human blood or blood treated with either aurintricarboxylic acid (ATA, 0.5 mg/mL; GPIb inhibitor), SC52012A (SC, 0.2 μg/mL; GPIIb/IIIa antagonist, G.D. Searle & Co. of Chicago, Ill.), or both. Thus, experimental groups received either 500 mg of ATA, 200 μg of SC52012A, or both drugs added to fresh human blood perfusate (pooled from three donors) prior to lung perfusion, while control groups received unmodified blood.

Pulmonary vascular resistance (PVR) was calculated from pulmonary artery land vein pressures and flow. Pulmonary vein effluent was collected serially for comparison of complement activation (C3a), mast cell activation (histamine) and thromboxane production ($TXB_2$) between groups. Survival endpoints were loss of transpulmonary flow, loss of oxygenation across the lungs, frank tracheal edema, and loss of perfusate volume (~1L) into lung parenchyma.

Results of Examples 1–3

ATA or SC alone blunted the rise in thromboxane, histamine, and PVR; median survival was prolonged from 12 to 25 min (p<0.005). Combined therapy yielded 165 min median survival (range 55–240;p<0.005 vs ATA or SC) and was associated with significantly decreased complement activation. Platelet sequestration at 10 min was 89% for controls, 51% for ATA, 7:0% for SC, and 28% for ATA+SC. Control exhibited an immediate rise in PVR, fluid sequestration in the lung, and without exception, cessation of oxygen transport function or transpulmonary flow within 15 minutes.

The results of Examples 1–3 are summarized in Table 1 immediately below:

TABLE 1

|  | Median Survival in min (95% conf int) | PVR, 5 min, cm H₂O/ mL/min (Mean ± SEM) | ΔC3a, 1 min, μg/mL (Mean ± SEM) | ΔC3a, 10 min, μg/mL (Mean ± SEM) | Δhistamine, 10 min, nM (Mean ± SEM) | ΔTXB₂, 10 min, ng/mL (Mean ± SEM) |
|---|---|---|---|---|---|---|
| Control | 10 (5–13) | 0.62 (.12) | 2.24 (0.53) | 2.71 (0.52) | 103 (21) | 25.4 (11) |
| Example 1 ATA | 25* (25–45) | 0.09* (.02) | 0.30* (0.11) | 1.81 (0.28) | 33* (8) | 4.6* (1.6) |
| Example 2 SC | 25* (15–40) | 0.10* (.02) | 1.96 (0.42) | 2.59 (0.42) | 32* (15) | 15.8 (2.0) |
| Example 3 ATA + SC | 165*#+ (55–240) | 0.11* (0.2) | 0.11*+ (.07) | 0.23*#+ (0.15) | 46* (15) | 17.0 (3.7) |

*p 0.05 against control group
p 0.05 against ATA group
+p 0.05 against SC group Summary of Examples 1–3

Inhibition of either GPIb or GPIIb/IIIa significantly attenuates PVR rise and mast cell activation in this HAR model; GPIb mediated interactions are particularly important to $TXB_2$ elaboration. When ATA, or ATA and SC are added, activation of complement is consistently blunted. When both the GPIb (ATA) and the GPIIb/IIIa (SC) axes of platelet interaction are blocked, graft survival is further prolonged, and complement activation is further inhibited beyond the effect observed with ATA alone. This finding demons it rates that interaction between platelets and porcine endothelium plays a role in the pace and character of lung HAR, that inhibition of platelet activity facilitates clinically useful graft function, and that platelet inhibition is synergistic with complement inhibition alone.

Examples 4 and 5

In Vitro Activation of Complement by Zymosan and Cobra Venom Factor

Platelet poor plasma (PPP—Example 4) and platelet rich plasma (PRP—Example 5) was prepared from human heparinized blood. Human plasma was treated with with ATA (0.5 mg/ml), SC (0.5 μg/ml), ATA+SC, bivalirudin (HIRULOG®, 0.1 g/L), or water (negative control) and then incubated in presence of zymosan (10 mg/mL) or cobra venom factor (CVF, 1 or 5 U/mL) to activate complement (negative control is water), for one hour at 37° C. with shaking. Then, the samples were subjected to centrifugation at 10,000 g for 45 minutes. The supernatant was then frozen in small aliquots at −70° C. C3a and C5b-9 levels were then assayed using commercial ELISA kits (Quidel). Results are presented in Table 2 immediately below.

TABLE 2

|  | Water | CVF 1U | CVF 5U | Zymosan | C3a ng/mL | Mean | Std Dev | C5b-9 (ng/ml) | Mean | Std Dev |
|---|---|---|---|---|---|---|---|---|---|---|
| Example 4 ZYMOSAN IV PPP | | | | | | | | | | |
| ATA | | | | | | | | | | |
| 1 | 16 | | | | 195 | | | | | |
| 2 | 250 | | | | 205 | 200 | 7 | 102 | 102 | |
| 3 | | 16 | | | 240 | | | | | |
| 4 | | 16 | | | 195 | 218 | 32 | 128 | 128 | |
| 5 | | | | 250 | 310 | | | | | |
| 6 | | | | 250 | 320 | 315 | 7 | 267 | 267 | |
| SC | | | | | | | | | | |
| 7 | 16 | | | | 440 | | | | | |
| 8 | 16 | | | | 475 | 458 | 25 | 141 | 141 | |
| 9 | | 16 | | | 2100 | | | 965 | | |
| 10 | | 16 | | | 1375 | 1738 | 513 | 955 | 960 | |
| ATA/SC | | | | | | | | | | |
| 11 | 16 | | | | 150 | | | | | |
| 12 | 80 | | | | 165 | 158 | 11 | 90 | 90 | |
| 13 | | 16 | | | 195 | | | | | |
| 14 | | 16 | | | 195 | 195 | 0 | 142 | 142 | |
| 15 | | | 80 | | 180 | | | | | |
| 16 | | | 80 | | 195 | 188 | 11 | 267 | 267 | |
| Water | | | | | | | | | | |
| 17 | 16 | | | | 445 | | | | | |
| 18 | 250 | | | | 455 | 450 | 7 | 119 | 119 | |
| 19 | | 16 | | | 1375 | | | 729 | | |
| 20 | | 16 | | | 1900 | 1638 | 371 | 939 | 834 | 148 |
| 21 | | | 80 | | 4850 | | | 4112 | | |
| 22 | | | 80 | | 7400 | 6125 | 1803 | 4452 | 4282 | 240 |

TABLE 2-continued

| | Water | CVF 1U | CVF 5U | Zymosan | C3a ng/mL | Mean | Std Dev | C5b-9 (ng/ml) | Mean | Std Dev |
|---|---|---|---|---|---|---|---|---|---|---|
| 23 | | | | 250 | 855 | | | | | |
| 24 | | | | 250 | 855 | 855 | 0 | 2428 | 2428 | |
| HIRULOG ® | | | | | | | | | | |
| 25 | 16 | | | | 590 | | | | | |
| 26 | 16 | | | | 505 | 548 | 60 | 26 | 26 | |
| 27 | | 16 | | | 1250 | | | 890 | | |
| 28 | | | 16 | | 1450 | 1350 | 141 | 943 | 917 | 37 |

Example 5
ZYMOSAN IV PRP

ATA

| 29 | 16 | | | | 165 | | | | | |
| 30 | 250 | | | | 150 | 158 | 11 | 142 | 142 | |
| 31 | | 16 | | | 165 | | | | | |
| 32 | | | 16 | | 165 | 165 | 0 | 173 | 173 | |
| 33 | | | | 250 | 290 | | | | | |
| 34 | | | | 250 | 235 | 263 | 39 | 249 | 249 | |

S/C

| 35 | 16 | | | | 530 | | | | | |
| 36 | 16 | | | | 490 | 510 | 28 | 146 | 146 | |
| 37 | | 16 | | | 1950 | | | | | |
| 38 | | | 16 | | 1950 | 1950 | 0 | 1030 | 1030 | |

ATA/SC

| 39 | 16 | | | | 160 | | | | | |
| 40 | 80 | | | | 145 | 153 | 11 | 125 | 125 | |
| 41 | | 16 | | | 200 | | | | | |
| 42 | | | 16 | | 250 | 225 | 35 | 170 | 225 | |
| 43 | | | | 80 | 200 | | | | | |
| 44 | | | | 80 | 140 | 170 | 42 | 283 | 283 | |

Water

| 45 | 16 | | | | 470 | | | | | |
| 46 | 250 | | | | 530 | 500 | 42 | 98 | 98 | |
| 47 | | 16 | | | 1400 | | | | | |
| 48 | | | 16 | | 1400 | 1400 | 0 | 832 | 832 | |
| 49 | | | | 80 | 9100 | | | 5719 | | |
| 50 | | | | 80 | 9800 | 9450 | 495 | 5584 | 5652 | 95 |
| 51 | | | | 250 | 970 | | | | | |
| 52 | | | | 250 | 1005 | 988 | 25 | >1000 | >1000 | |

HIRULOG ®

| 53 | 16 | | | | 490 | | | | | |
| 54 | 16 | | | | 380 | 435 | 78 | 126 | 126 | |
| 55 | | 16 | | | 1800 | | | | | |
| 56 | | | 16 | | 1500 | 1650 | 212 | 842 | 842 | |

Examples 4 and 5
Zymosan IV
Methods:
PRP 15 min @ 280 g (10 min @ 90 g)
PPP 10 min @ 2400 g (RT)
CVF 1 Ul and 5 Ul/mL (from 62 Ul/mL stock)
Zymosan 50 mg/mL
ATA 0.7 mg/mL (from 100 mg/mL stock)
SC 1/1000 dilution of stock
HIRULOG ® 0.1 g/L (1/100 dilution of 10 g/L stock)

Since the ATA compound has an anti-complement activity by itself, as was seen in in the ex vivo lung perfusion experiments of Examples 1–3 (Table 1), and in the in vitro experiments of Examples 4 and 5 (Table 2), different platelet modulators were evaluated in accordance with the present invention (Examples 6 and 7).

Example 6

Flow Chamber Assay

A parallel plate flow chamber was used to expose pig endothelial cells (EC) to human blood under laminar flow conditions (shear rate 550/s). Blood was either untreated, or treated with platelet GPIb and GPIIb/IIIa receptor inhibitors. In one experimental sample the GPIb and GPIIb/IIIa inhibitors comprised ATA at a concentration of 0.5 mg/ml and SC52012A (SC, 0.5 µg/ml). In the other experimental sample a monoclonal antibody to GPIb (1.0 µg/ml) was combined with RHEOPRO® GPIIb/IIIa monoclonal antibody inhibitor at a concentration of 40 µg/ml. Complement activation was evaluated by measurement of C3a production before, and 15 and 30 minutes, after the circulation was started through the flow chamber.

Figure 1B:
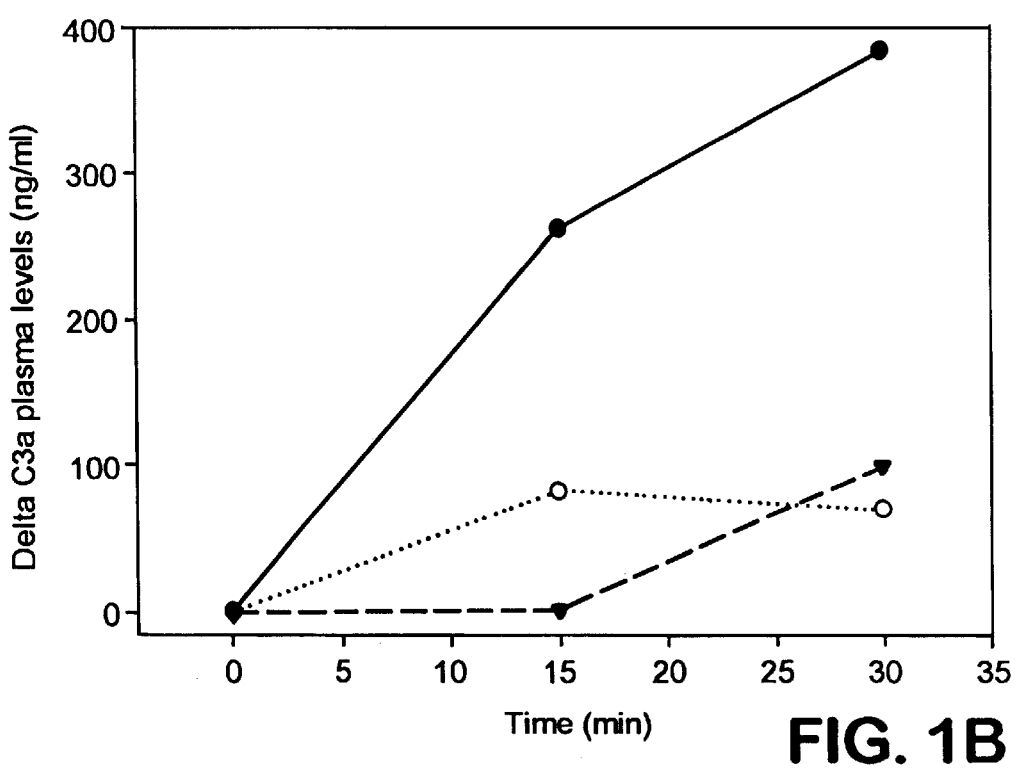

Results are presented in FIGS. 1A and 1B, and are shown as C3a levels act given time points minus C3a of baseline (delta) in two independent experiments. As seen previously in the lung perfusion experiments described in Examples 1–3 above, ATA+SC significantly decreased complement activation in a xenogeneic environment. Blockade of GPIb and GPIIbIIIa through the use of specific monoclonal antibodies also significantly delays complement activation, as shown in FIG. 1A, and can prevent it substantially to the same extent as ATA+SC, as shown in FIG. 1B.

It is noted that the synergistic effect of GPIb and GPIIbIIIa inhibitors is demonstrated in this Example. Because this effect is obtained using entirely different, non-chemical reagents, this Example shows that the effect on inhibiting platelet activation is specific to inhibition of platelet receptors, and is not only a consequence of a chemical property of ATA or SC affecting another pathway or molecule.

Example 7

Direct Thrombin Inhibition with Bivalirudin

Materials and Methods

In an established in situ, ex vivo model, piglet lungs were perfused with either heparinized (3,000 U/L) human blood or with blood additionally pretreated with 140 mg/L of bivalirudin (a semisynthetic analogue of hirudin). Pulmonary vein effluent was collected serially for measurement of complement activation (C3a), mast cell activation (histamine), and thrombin formation (F1+2). Survival endpoints were loss of transpulmonary blood flow, loss of oxygenation across the lungs, and sequestration of perfusate volume (~1 L) into the lung. Statistical comparisons were made using the 2-tailed t-test.

Results

Results are summarized in Table 3. Bivalirudin limited thrombin production more than 90% (as measured by F1+2) and was associated with significantly improved mean survival, from 8 to 77 minutes. The rise in PVR and histamine release was significantly decreased with bivalirudin. Complement activation and intrapulmonary platelet sequestration also were significantly blunted with bivalirudin.

Example 8

Ex Vivo Perfusion Of Kidneys Method Of Kidney Perfusion

In accordance with the present invention, kidney perfusion is perfomed to analyze the role of platelet activation and aggregation in hyperacute rejection of a pig kidney by human blood. Outbred piglets (4–6 kg) are used in an established in situ ex vivo isolated kidney perfusion model using a mechanical perfusion circuit with pressure and flow monitoring. Piglet kidneys are perfused with unmodified human blood or blood treated with either aurintricarboxylic acid (ATA, 0.5 mg/mL; GPIb inhibitor), SC52012A (SC, 0.2 $\mu$g/mL; GPIb/IIIa antagonist, G.D. Searle & Co. of Chicago, Ill.), or both. Thus, experimental groups receive either 500 mg of ATA, 200 $\mu$g of SC52012A, or both drugs added to fresh human blood perfusate (pooled from three donors) prior to kidney perfusion, while control groups receive unmodified blood.

Renal vascular resistance (PVR) is calculated from renal artery and vein pressures and flow. Renal vein effluent is collected serially for comparison of complement activation (C3a), mast cell activation (histamine) and thromboxane production (TXB2) between groups. Survival endpoints are loss of transkidney flow, decrease or loss of urine production by the kidneys, frank parenchymal hemorrhage, and loss of perfusate volume (~1L) into kidney parenchyma.

Example 9

Flow Chamber Assay—Individual Receptor Blockade

Experiments in which GPIb and GPIIbIIIa platelet receptors are blocked individually and together in a flow chamber model are also performed to further characterize platelet inhibition and therefore complement inhibition with the combined strategies in accordance with the present invention. The flow chamber model of Example 6 is employed.

REFERENCES

The references listed below as well as all references cited in the specification are incorporated herein by reference to

TABLE 3

| | Survival Min (± SEM) | ΔF1 + 2 10 min nM (± SEM) | PVR cm H$_2$O/mL/ min 5 min (± SEM) | ΔC3a 1 min $\mu$g/ml (± SEM) | ΔC3a 10 min $\mu$g/ml (± SEM) | Δ histamine 10 min nM (± SEM) | Platelets 10 min (± SEM) |
|---|---|---|---|---|---|---|---|
| Control | 8 (1) | 5.3 (4) | 0.62 (.12) | 2.24 (1.5) | 2.71 (1.3) | 106 (21) | 13k (2k) |
| Bivali-rudin | 77 (22)* | 0.5 (0.8)* | 0.16 (.05)* | 0.82 (0.8)* | 1.97 (1) | 21 (4)* | 39k (5k)* |

F1 + 2 indicates thrombin formation; C3a complement activation and the riseabove baseline values. -*p < .05 against control group.

This Example shows that by inhibiting thrombin (e.g. via bivalirudin sold under the registered trademark HIRULOG®), complement activation is unexpectedly inhibited, and survival is significantly prolonged. This activity may occur indirectly by reducing the interaction of thrombin with its receptors on platelets, and may reduce complement activation by its effect on inhibiting platelet activation. This effect supports the prior Examples showing that inhibition of platelets inhibits complement activation. This Example predicts that thrombin inhibition specifically and inhibition of coagulation generally can be used to control complement activation in HAR of the lung.

the extent that they supplement, explain, provide a background for or teach methodology, techniques and/or compositions employed herein.

Allen, et al., 1993. *Circulation* 88, pp. 243.
Ammerer, 1983. *Meth Enzymol* 101, pp. 192.
Auchincloss, 1988. *Transplantation* 46, pp. 1.
Ausubel, et al., 1992. *Current Protocols in Mol Bio*, John Wiley & Sons, New York.
Berg, et al., 1991. *J Biol Chem* 23, pp. 14869.
Bevilacqua, et al., 1989. *Science* 243, pp. 1160.
Bevilacqua and Nelson, 1993. *J Clin Invest* 91, pp. 379.
Bockenstedt, et al., *J. Clin. Invest.* 77: 743, (1986)

Bodanszky, et al., "Peptide Synthesis", John Wiley & Sons, Second Edition, 1976
Bode, A. P., et al., *J. Lab. Clin. Res.* 113(1):94–104 (1989).
Bradley, in Robertson (ed), 1987. *Teratocarcinomas and Embryonic Stem Cells a Practical Approach*. IRL Press, Eynsham, Oxford, England.
Brinster, et al., 1989. *Proc Natl Acad Sci* 86, pp. 7087–7091.
Brinster, et al., 1985. *Proc Natl Acad Sci* 82, pp. 4438–4442.
Brockmeyer, et al., 1993. *Transplantation* 55, pp. 610.
Brugge man, N. and Neuberger, M., *Nature* 386(6620):25–6 (March 1997).
Bruggeman, N. and Neuberger, M. S., *Immunol. Today* 17(8):391–7 (August 1996).
Campbell, K. H., *Semin. Cell Dev. Biol.* 10(3):245–52 (June 1999)
Capecchi, 1989. *Trends in Genetics* 5(3) pp. 70–76.
Carlos, et al., 1991. *Blood* 77, pp. 2266.
Carson, et al., 1993. *J Rheumatol* 20, pp. 809.
Chang, et al., 1978. *Nature* 275, pp. 615.
Chomczynski and Sacchi, 1987. *Analytical Biology* 162, pp. 156.
Cibelli, J. B., et al., *Science* 280(5367):1256–8 (May 22, 1998)
Clackson, et al., 1991. *Nature* 352, pp. 624–628.
Coligan, et al., 1992. *Current Protocols in Immunol*, John Wiley & Sons, New York.
Cotran, et al., 1986. *J Exp Med* 164, pp. 661.
Dalmasso, et al., 1992. *Am J Path* 140, pp. 1157.
Davis, et al., 1991. *Science* 253, pp. 59.
Deutscher (ed), 1990. *Guide to Protein Purification*, Volume 182. Academic Press, Inc., San Diego, Calif.
Dulbecco et al., *Virol* 8:396 (1959)
Eguchi, et al., 1991. *Annu Rev Biochem* 60, pp. 631–652.
Evans and Scarpulla, 1989. *Gene* 84, pp. 135.
Ferran, et al., 1993. *Transplantation* 55, pp. 605.
Fields et al., *Int. J. Peptide Protein Res.*, 35:161–214,1990
Fries, et al., 1993. *Am Journ Pathol* 143:, pp. 725.
Frohman and Martin, 1989. *Cell* 56, pp. 145–147.
Gearing and Newman, 1993. *Immunol Today* 14(10), pp. 506.
Gearing, et al., 1992. *Annals NY Acad Sci* 667, pp. 324.
Georas, et al., 1992. *Am J Respir Cell Mol Biol* 7, pp. 261.
Gilbert, 1984. *Proc Natl Acad Sci* 81, pp. 1991.
Goeddel, et al., 1980. *Nucl Acids Res* 8, pp. 4057.
Goeddel (ed), 1990. *Gene Expression Technology*, Volume 185. Academic Press, Inc., San Diego, Calif.
Gossler, et al., 1986. *Proc Natl Acad Sci* 83, pp. 9065–9069.
Graber, et al., 1990. *J Immunol* 145, pp. 819.
Haber, 1992. *Immunol Rev* 130, pp. 189–212.
Hakkert, et al., 1991. *Blood* 78, pp. 2721.
Harlow and Lane, 1988. *Antibodies: A Laboratory Manual*, Cold Spring Harbor Laboratory, Cold Spring Harbor, N.Y.
Harris: and Angal (eds), 1989. *Protein Purification Methods: A Practical Approach*. IRL Press, Oxford University Press, Oxford.
Hasty, et al., 1991. *Mol Cell Bio* 11 (11), pp. 5586–5591.
Hogan, et al., 1986. *Manipulating the Mouse Embryo: A Laboratory Manual*. Cold Spring Harbor Laboratory, Cold Spring Harbor, N.Y.
Hollopeter, G., et al., *Nature* 409:202–207 (Jan. 11, 2001).
Holmsen, H., *Thromb. Haemostas.* 98:1030–1041 (1977).
Huse et al., *Science* 246:1275–1281 (1989)
J. F. W. McOmie, "Protective Groups in Organic Chemistry", Plenum Press, New York, 1973
Jakobvits, A., *Curr. Opin. Biotechnol.* 6(5):561–6.
Jasin and Berg, 1988. *Genes & Development* 2, pp. 1353–1363.
Jeannotte, et al., 1991. *Mol Cell Bio* 11(11), pp. 5578–5585.
King, S. B. and Mahmud, E., *Circulation* 2466–2468 (Dec. 21/28, 1999).
Koch, et al., 1991. *Lab Invest* 64, pp. 313.
Kohler and Milstein, *Nature* 256:495–497 (1975)
Kuijpers, et al., 1991. *J Immunol* 147, pp. 1369.
Larigan, et al., 1992. *DNA Cell Biol* 206, pp. 401.
Lasky, 1992. *Science* 258, pp. 964.
Leeuwenberg, et al., 1992. *Immunology* 77, pp. 543.
Leventhal, et al., 1993. *Transplantation* 55, pp. 857.
Lidell and Cryer, 1991. *A Practical Guide To Monoclonal Antibodies*. John Wiley & Sons, Chichester, West Sussex, England.
Lo, et al., 1991. *J Exp Med* 173, pp. 1493.
Lobb, et al., 1991. *J Immunol* 147, pp. 124.
Longberg, N. and Huszar, D., *Int. Rev. Immunol.* 13(1): 65–93 (1995).
Lovell-Badge, in Robertson (ed), 1987. *Teratocarcinomas and Embryonic Stem Cells a Practical Approach*. IRL Press, Eynsham, Oxford, England.
Luckow, et al., 1988. *Bio/Technology* 6, pp. 47.
Makowka, et al., September 1993 *Second International Congress on Xenotransplantation*, Cambridge, England, abstract 4.
Maniatis, 1982. *Molecular Cloning: A Laboratory Manual*. Cold Spring Harbor Laboratory, Cold Spring Harbor, N.Y., pp. 412.
Mansour, et al., 1988. *Nature* 336, pp. 348–352.
McMahon, et al, 1990. *Cell* 62, pp. 1073–1085.
Meienhofer, J., "Hormonal Proteins and Peptides", Vol. 2, p. 46, Academic Press (New York), 1983
Mejia-Laguna, et al., 1972. *Am Journ Pathol* 69, pp. 71.
Merrifield, *Adv Enzymol*, 32:221–96, 1969
Moir, et al., 1991. *Meth Enzymol* 194, pp. 491–507.
Mollnes, et al., 1988. *Scand J Inunol* 28, pp. 307–312.
Montgomery, et al., 1991. *Proc Natl Acad Sci* 88, pp. 6523.
Montz, et al., 1990. *Cellular Immunol* 127, pp. 337–351.
Morrison, 1992. *Annu Rev Immunol* 10, pp. 239–265.
Mortensen, et al., 1992. *Mol Cell Bio* 12(5), pp. 2391–2395.
Muler-Eberhard, 1988. *Ann Rev Biochem* 57, pp. 321.
Mulligan, et al., 1991. *J Clin Invest* 88, pp. 1396.
Mulligan, et al., 1993. *J Immunol* 151, pp. 6410.
Najarian, 1992. *Transplant Proc* 24, pp. 733.
Newman, et al., 1993. *J Immunol* 150, pp. 633.
Nguyen, H., et al., *Microbiol. Immunol.* 41(12):901–7 (1997).
PCT Publication No. WO 93/02188
PCT Publication No. WO 92/11757
PCT Publication No. WO 90/08832
PCT Publication No. WO 96/38543
Pedersen, et al., 1990. *Transgenic Techniques in Mice—A Video Guide*. Cold Spring Harbor Laboratory, Cold Spring Harbor, N.Y.
Picker, et al., 1991. *Nature* 349, pp. 796.
Pigott, et al., 1992. *Biochem Biophys Res Commun* 187, pp. 584.
Pruitt, et al., 1991. *Transplantation* 52, pp. 868.
Redi, et al., 1991. *Am J Pathol* 139, pp. 461.
Reetsma, K., et al., 1964, *Ann. Surg.* 160:384
Reichmann, et al., 1988. *Nature* 332, pp. 323–327.
*Remington's Pharmaceutical Sciences*. 17th Ed., 1985. Mack Publishing Company, Philadelphia, Pa.
Robertson, et al., 1986. *Nature* 323, pp. 445–448.
Robertson, in Robertson (ed), 1987. *Teratocarcinomas and Embryonic Stem Cells a Practical Approach*. IRL Press, Eynsham, Oxford, England.
Rodrigues, et al., 1993. *J Immunol* 151, pp. 6954–6961.

Sambrook, et al., 1989. *Molecular Cloning: A Laboratory Manual*. 2nd Ed. Cold Spring Harbor Laboratory Press, Cold Spring Harbor, N.Y.
Sanger, et al., 1977. *Proc Natl Acad Sci USA* 74, pp. 5463.
Sastry, et al., *Proc Natl Acad Sci USA* 86:5728–5732 (1989)
Satake, et al., September 1993. *Second International Congress on Xenotransplantation*, Cambridge, England, abstract 126.
Schena, et al., 1991. *Meth Enzymol* 194, pp. 389–398.
Schnieke, A. E., et al., *Science* 278(5346):2130–3 (Dec. 19, 1997)
Schroder et al., "*The Peptides*", Vol. 1, Academic Press (New York), 1965
Shimuzu, et al., 1991. *Nature* 349, pp. 799.
Somervile and d'Apice, 1993. *Kidney Intl* 44, pp. 112.
Steward iet al., "*Solid Phase Peptide Synthesis*", W. H. Freeman Co., San Francisco, 1969
Sundsmo, J. S., et al., *Clin Immunol Immunopathol* 35(2): 211–25 (May 1985).
Taylor, et al., 1992. *Transplantation* 54, pp. 451.
Thomas, et al., 1986. *Cell* 44(3), pp. 419–428.
Thomas, et al., 1987. *Cell* 51(3), pp. 503–512.
Thomas, et al., 1992. *Mol Cell Bio* 12(7), pp. 2919–2923.
Tibell, et al., September 1993. *Second International Congress on Xenotransplantation*, Cambridge, England, abstract 64.
Tuso, et al., 1993. *Transplantation* 55, pp. 1375.
Tyrrell, et al., 1991. *Proc Natl Acad Sci* 88, pp. 10372.
U.S. Pat. No. 5,424,334
U.S. Pat. No. 5,409,939
U.S. Pat. No. 5,504,106
U.S. Pat. No. 5,441,974
U.S. Pat. No. 4,244,946
U.S. Pat. No. 6,008,193
U.S. Pat. No. 5,976,532
U.S. Pat. No. 5,973,003
U.S. Pat. No. 5,886,208
U.S. Pat. No. 5,858,972
U.S. Pat. No. 5,849,702
U.S. Pat. No. 5,849,536
U.S. Pat. No. 5,837,488
U.S. Pat. No. 5,811,398
U.S. Pat. No. 5,798,370
U.S. Pat. No. 5,731,324
U.S. Pat. No. 5,721,366
U.S. Pat. No. 5,705,890
U.S. Pat. No. 5,703,125
U.S. Pat. No. 5,674,894
U.S. Pat. No. 5,652,363
U.S. Pat. No. 5,646,183
U.S. Pat. No. 5,618,843
U.S. Pat. No. 5,612,355
U.S. Pat. No. 5,602,155
U.S. Pat. No. 5,552,431
U.S. Pat. No. 5,543,425
U.S. Pat. No. 4,616,034
U.S. Pat. No. 5,489,594
U.S. Pat. No. 5,481,021
U.S. Pat. No. 4,758,573
U.S. Pat. No. 5,430,043
U.S. Pat. No. 5,223,539
U.S. Pat. No. 4,719,220
U.S. Pat. No. 5,378,727
U.S. Pat. No. 5,360,907
U.S. Pat. No. 5,354,738
U.S. Pat. No. 5,344,957
U.S. Pat. No. 5,344,837
U.S. Pat. No. 5,302,601
U.S. Pat. No. 5,264,457
U.S. Pat. No. 5,262,426
U.S. Pat. No. 5,260,203
U.S. Pat. No. 5,254,573
U.S. Pat. No. 5,227,384
U.S. Pat. No. 5,019,581
U.S. Pat. No. 5,220,050
U.S. Pat. No. 5,208,242
U.S. Pat. No. 5,091,396
U.S. Pat. No. 5,053,393
U.S. Pat. No. 5,037,808
U.S. Pat. No. 4,990,518
U.S. Pat. No. 4,988,707
U.S. Pat. No. 4,962,106
U.S. Pat. No. 4,914,108
U.S. Pat. No. 4,880,788
U.S. Pat. No. 4,857,508
U.S. Pat. No. 5,625,125
U.S. Pat. No. 5,614,396
U.S. Pat. No. 5,489,742
U.S. Pat. No. 4,736,866
U.S. Pat. No. 5,741,957
U.S. Pat. No. 5,550,316
U.S. Pat. No. 5,648,061
U.S. Pat. No. 4,873,191
U.S. Pat. No. 5,166,065
U.S. Pat. No. 5,032,407
U.S. Pat. No. 5,573,933
U.S. Pat. No. 5,162,215
Vercellotti, et al., 1991. *J Immunol* 146, pp. 730.
Walker, *Int. Archs. Allergy Appl. Immunology* 60:44–49 (1979)
Weller, et al., 1992. *J Biol Chem* 267, pp. 15176.
Winter and Milstein, 1991. *Nature* 349, pp. 293–299.
Wurzner, et al., 1991. *Complement Inflamm* 8, pp. 328–340.
Zehr, et al., 1994. *Transplantation* 57, pp. 900.
Zimmer et al., *Peptides* 1992, pp. 393–394, ESCOM Science Publishers, B. V., 1993
Zola, *Monoclonal Antibodies: a Manual of Techniques*, CRC Press, Inc. (1987)

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of inhibiting complement activation in a warm-blooded vertebrate in which said inhibition is desired, the method comprising administering a therapeutically effective amount of a platelet activity modulator to a warm-blooded vertebrate, wherein the platelet activity modulator comprises a combination of a first composition comprising a GPIb inhibitor and a second composition comprising a GPIIb/GPIIIa inhibitor, whereby complement activation is inhibited.

2. A method of inhibiting complement activation by a transplanted tissue in a warn-blooded vertebrate, the method comprising administering a therapeutically effective amount of a platelet activity modulator to a warm-blooded vertebrate before, during or after a tissue is transplanted to the warm-blooded vertebrate, wherein the platelet activity modulator comprises a combination of a first composition comprising a GPIb inhibitor and a second composition comprising a GPIIb/GPIIIa inhibitor, whereby complement activation by the transplanted tissue is inhibited.

3. The method of claim 1, wherein the GPIb inhibitor comprises aurin tricarboxylic acid.

4. The method of claim 1, wherein the GPIb inhibitor comprises an antibody that blocks GPIb activity.

5. The method of claim 1, wherein the GPIIb/GPIIIa inhibitor comprises SC52012A.

6. The method of claim 1, wherein the GPIIb/GPIIIa inhibitor comprises an antibody that blocks GPIIb/GPIIIa activity.

7. The method of claim 1, wherein the therapeutically effective amount of the platelet activity modulator ranges from about 0.01 mg to about 10,000 mg per day.

8. The method of claim 7, wherein the therapeutically effective amount of the platelet activity modulator ranges from about 0.1 mg to about 1,000 mg per day.

9. The method of claim 8, wherein the therapeutically effective amount of the platelet activity modulator ranges from about 1 mg to about 300 mg per day.

10. The method of claim 2, wherein the GPIb inhibitor comprises aurin tricarboxylic acid.

11. The method of claim 2, wherein the GPIb inhibitor compnses an antibody that blocks GPIb activity.

12. The method of claim 2, wherein the GPIIb/GPIIIa inhibitor comprises SC52012A.

13. The method of claim 2, wherein the GPIIb/GPIIIa inhibitor comprises an antibody that blocks GPIb/GPIIIa activity.

14. The method of claim 2, wherein the therapeutically effective amount of the platelet activity modulator ranges from about 0.01 mg to about 10,000 mg per day.

15. The method of claim 14, wherein the therapeutically effective amount of the platelet activity modulator ranges from about 0.1 mg to abouti 1,000 mg per day.

16. The method of claim 15, wherein the therapeutically effective amount of the platelet activity modulator ranges from about 1 mg to about 300 mg per day.

17. The method of claim 2, wherein the transplanted tissue is a vascularized tissue.

18. The method of claim 17, wherein the vascularized tissue is selected from the group consisting of heart, lung, liver, kidney, pancreas and combinations thereof.

19. The method of claim 2, wherein the transplanted tissue is a xenongrft tissue.

20. The method of claim 19, wherein the xenograft tissue is a vascularized xenograft tissue.

21. The method of claim 20, wherein the vascularized xenograft tissue is selected from the group consisting of heart, lung, liver, kidney, pancreas and combinations thereof.

* * * * *